United States Patent
Capriotti et al.

(10) Patent No.: US 12,044,833 B2
(45) Date of Patent: Jul. 23, 2024

(54) THERMAL IMAGING ENDOSCOPE

(71) Applicant: The Regents of the University of California, Oakland, CA (US)

(72) Inventors: Margherita Capriotti, La Jolla, CA (US); Andrew Vahabzadeh-Hagh, La Jolla, CA (US); Lauren Waller, La Jolla, CA (US); Brandon Hong, La Jolla, CA (US); Utkrisht Rajkumar, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 464 days.

(21) Appl. No.: 17/603,282

(22) PCT Filed: Apr. 10, 2020

(86) PCT No.: PCT/US2020/027794
§ 371 (c)(1),
(2) Date: Oct. 12, 2021

(87) PCT Pub. No.: WO2020/210717
PCT Pub. Date: Oct. 15, 2020

(65) Prior Publication Data
US 2022/0221696 A1 Jul. 14, 2022

Related U.S. Application Data

(60) Provisional application No. 62/833,509, filed on Apr. 12, 2019.

(51) Int. Cl.
*G02B 13/14* (2006.01)
*A61B 1/04* (2006.01)
*A61B 1/06* (2006.01)
*G02B 13/00* (2006.01)
*G02B 23/24* (2006.01)
*G02B 27/10* (2006.01)

(52) U.S. Cl.
CPC .............. *G02B 13/14* (2013.01); *A61B 1/042* (2013.01); *A61B 1/0669* (2013.01); *G02B 13/0095* (2013.01); *G02B 23/2461* (2013.01); *G02B 27/1013* (2013.01)

(58) Field of Classification Search
None
See application file for complete search history.

(56) References Cited

U.S. PATENT DOCUMENTS 6,638,216 B1  10/2003  Durell
6,898,458 B2   5/2005  Zeng et al.
(Continued)

OTHER PUBLICATIONS

International Search Report and Written Opinion for International Patent Application No. PCT/US2020/027794. Mail Date: Jul. 1, 2020. 29 pages.

*Primary Examiner* — Robert E. Tallman
(74) *Attorney, Agent, or Firm* — Perkins Coie LLP

(57) ABSTRACT

Described are devices, systems and methods for thermographic imaging of conditions of the ear, nose, and throat (ENT). An example device for thermographic ENT imaging includes an endoscope and a thermal imaging camera that can be either integrated or added as an attachment to the endoscope. The device may also include a mirror configured to direct thermal radiation emitted by a target area to the thermal imaging camera.

20 Claims, 18 Drawing Sheets

(56) References Cited

U.S. PATENT DOCUMENTS

2005/0182321 A1\* 8/2005 Frangioni ............ A61B 5/0071
                                                          600/431
2009/0187072 A1   7/2009 Manohara et al.
2014/0107413 A1   4/2014 Tremaglio et al.
2016/0286187 A1   9/2016 Takenaga et al.

\* cited by examiner

THERMAL IMAGING ENDOSCOPE

CROSS-REFERENCE TO RELATED APPLICATIONS

This patent document is a 371 National Phase Application of International Application No. PCT/US2020/027794, filed on Apr. 10, 2020, which claims the benefit of U.S. Provisional Patent Application No. 62/833,509 entitled "THERMAL ENDOSCOPE FOR CLINICAL DIAGNOSTICS," and filed on Apr. 12, 2019. The entire contents of the aforementioned patent applications are incorporated herein by reference in their entireties.

TECHNICAL FIELD

This patent document relates to the use of infrared thermography in otorhinolaryngological endoscopy for diagnosing and treating conditions of the ear, nose, and throat (ENT).

BACKGROUND

Endoscope is an instrument used to examine the interior of a hollow organ or cavity of a body. Endoscopes are inserted directly into an organ which needs examination during an endoscopy procedure.

SUMMARY

There is a clinical need for improved visual inspection for ENT diagnosis and surgeries. Endoscopy is often required to access locations of ENT conditions. However, assessment and identification of ENT abnormalities and pathologies remain challenging due to the difficult-to-reach ENT locations and the complex nature of many of the related pathologies. An imaging technique that could provide additional information, high-contrast and quantitative data about the patient condition will be useful, especially to assist ENT clinicians in diagnosis and surgeries and to avoid the need to resort to more expensive imaging techniques (e.g., computed tomography (CT) scans, ultrasound imaging, magnetic resonance imaging (MRI)).

This patent document discloses a thermographic system that can be integrated with endoscopes used in otolaryngology. The thermal imaging system can be directly integrated into an endoscope or, alternatively, designed as an add-on attachment to an endoscope. In either embodiment, the thermal imaging system can preserve normal imaging in a visible spectral range (referred to as visible-range below) function of the endoscope. The thermal imaging system can provide thermal images having the same field of view as that of the visible-range images, or the field of view in the thermal images can be larger or smaller than that of the visible-range images, depending on the needs of a particular application. The thermal camera (also referred to as thermal infrared imaging camera or thermal imaging camera or thermal-range camera)-enabled endoscope or an add-on thermal camera attachment to an endoscope will access the patient's nose or mouth through a rigid or flexible tube and transmit and/or record videos of the temperature distribution of a region of interest while simultaneously acquiring visible-spectrum images of the region. The acquired thermal-range and visible-range data can be processed and output in 1D, 2D, or 3D format and/or as a score showing, for example, severity of a disease on a scale from 1 to 10. Diagnostic procedures can involve analyzing the processed data using such metrics as temperature difference between a local area and neighboring areas, rate of temperature change in the local area as well as size, location, and features (e.g., shape of the edge) of the local area, among others.

In one aspect, the present patent document provides a thermal imaging system for imaging, diagnosing, or monitoring treatment of conditions of the human body, including ENT conditions. The thermal imaging system comprises an endoscope and a thermal infrared imaging camera. In one embodiment, the thermal imaging camera is integrated into the endoscope. In another embodiment, the thermal imaging camera is an add-on attachment to the endoscope.

In some aspects, the present patent document provides a thermal imaging system which includes one or more mirrors which can be used for adjusting direction of a field of view of the system and/or for directing light from a light source to a target area of interest. In other aspects, such field of view adjustments and/or changes of the direction of illumination can be done by means other that such mirror(s).

Embodiments of the technology disclosed herein can use different optical elements such as mirrors, dichroic mirrors, "hot" or "cold" mirrors, filters, beam splitters, among other optical elements.

In some aspects, the thermal imaging camera uses temperature as a contrast marker for lesions or abnormalities that have low contrast in a visible spectral range.

In another aspect, the present patent document provides a passive imaging modality adapted to be used in addition to or independent of line-of-sight visibility for external or internal inspection of the human body, through a natural orifice, surgically created openings, subdermal spaces, or laparoscopic applications.

In another aspect, the present patent document discloses an endoscope, comprising: a body having a proximal end and a distal end; a light source configured to emit light in a first range of wavelengths and attached to the body proximate to the proximal end of the body; a mirror attached to the body proximate to the distal end of the body; a hot mirror positioned proximate to the proximal end of the body and configured to reflect light in a second range of wavelengths and allow light in the first range of wavelengths to pass through the hot mirror; a first imaging system positioned proximate to the proximal end of the body and configured to create a first image of a target area using light in the first range of wavelengths; a second imaging system positioned proximate to the proximal end of the body and configured to create a second image of the target area using light in the second range of wavelengths; wherein: the mirror is configured to reflect light received by the mirror from the light source towards the target area, the mirror is configured to receive a first portion of light in the first range of wavelengths reflected by the target area and a second portion of light in the second range of wavelengths emitted by the target area and direct the first portion of light and the second portion of light towards the proximal end of the body, the hot mirror is configured to transmit at least a part of the first portion of light towards the first imaging system and reflect at least a part of the second portion of light towards the second imaging system. In some aspects, the hot mirror can be replaced by a "cold mirror" configured to transmit at least a part of the second portion of light towards the second imaging system and reflect at least a part of the first portion of light towards the first imaging system.

In another aspect, the present patent document discloses an endoscope, comprising: a first body having a proximal end and a distal end; a second body having a proximal end and a distal end, wherein the second body is attached to the first body such that the distal end of the second body is proximate to the distal end of the first body; a light source configured to emit light in a first range of wavelengths and attached to the first body proximate to the proximal end of the first body; a first mirror attached to the first body proximate to the distal end of the first body; a second mirror attached to the second body proximate to the distal end of the second body; a first imaging system positioned proximate to the proximal end of the first body; a second imaging system positioned proximate to the proximal end of the second body; wherein: the first mirror is configured to reflect light received by the first mirror from the light source towards a target area, the first mirror is configured to receive a first portion of light in the first range of wavelengths reflected by the target area and direct the first portion of light towards the proximal end of the first body, the second mirror is configured to receive a second portion of light in a second range of wavelengths emitted by the target area and direct the second portion of light towards the proximal end of the second body, the first imaging system is configured to receive at least a part of the first portion of light and create a first image of the target area corresponding to the first range of wavelengths, and the second imaging system is configured to receive at least a part of the second portion of light and create a second image of the target area corresponding to the second range of wavelengths.

In another aspect, the present patent document discloses an endoscope, comprising: a body having a proximal end and a distal end; a light source configured to emit light in a first range of wavelengths and attached to the body proximate to the proximal end of the body; a mirror attached to the body proximate to the distal end of the body; a first imaging system attached to the body proximate to the proximal end of the body; a second imaging system attached to the body proximate to the distal end of the body; wherein: the mirror is configured to reflect light received by the mirror from the light source towards a target area, the mirror is configured to receive a first portion of light in the first range of wavelengths reflected by the target area and direct the first portion of light towards the proximal end of the body, the first imaging system is configured to receive at least a part of the first portion of light and create a first image of the target area corresponding to the first range of wavelengths, and the second imaging system is configured to receive light emitted by the target area in a second range of wavelengths and create a second image of the target area corresponding to the second range of wavelengths.

In another aspect, the present patent document discloses an endoscope, comprising: a body having a proximal end and a distal end; and an imaging system attached to the body proximate to the distal end of the body; wherein the imaging system is configured to receive light emitted by a target area in a range of wavelengths and create an image of the target area corresponding to the range of wavelengths.

In another aspect, the present patent document discloses a method of fabrication of an endoscope, comprising: providing a body having a proximal end and a distal end; and coupling an imaging system to the body proximate to the distal end of the body; wherein the imaging system is capable of receiving light emitted by a target area in a range of wavelengths and creating an image of the target area corresponding to the range of wavelengths.

In another aspect, the present patent document discloses a method of fabrication of an endoscope, comprising: providing a body having a proximal end and a distal end; coupling a light source capable of producing light in a first wavelength band to the body proximate to the proximal end of the body; coupling a mirror to the body proximate to the distal end of the body; coupling a first imaging system to the body proximate to the proximal end of the body; coupling a second imaging system to the body proximate to the distal end of the body; wherein: the mirror is capable of reflecting light received by the mirror from the light source towards a target area, the mirror is capable of receiving a first portion of light in the first wavelength band reflected by the target area and directing the first portion of light towards the proximal end of the body, the first imaging system is capable of receiving at least a part of the first portion of light and creating a first image of the target area corresponding to the first wavelength band, and the second imaging system is capable of receiving light emitted by the target area in a second wavelength band and creating a second image of the target area corresponding to the second wavelength band.

In another aspect, the present patent document discloses a method of fabrication of an endoscope, comprising: providing a first body having a proximal end and a distal end; providing a second body having a proximal end and a distal end; coupling the second body to the first body such that the distal end of the second body is proximate to the distal end of the first body; coupling a light source capable of emitting light in a first range of wavelengths to the first body proximate to the proximal end of the first body; coupling a first mirror to the first body proximate to the distal end of the first body; coupling a second mirror to the second body proximate to the distal end of the second body; coupling a first imaging system to the first body proximate to the proximal end of the first body; coupling a second imaging system to the second body proximate to the proximal end of the second body; wherein: the first mirror is capable of reflecting light received by the first mirror from the light source towards a target area, the first mirror is capable of receiving a first portion of light in the first range of wavelengths reflected by the target area and directing the first portion of light towards the proximal end of the first body, the second mirror is capable of receiving a second portion of light in a second range of wavelengths emitted by the target area and directing the second portion of light towards the proximal end of the second body, the first imaging system is capable of receiving at least a part of the first portion of light and creating a first image of the target area corresponding to the first range of wavelengths, and the second imaging system is capable of receiving at least a part of the second portion of light and creating a second image of the target area corresponding to the second range of wavelengths.

In another aspect, the present patent document discloses a method of fabrication of an endoscope, comprising: providing a body having a proximal end and a distal end; coupling a light source capable of emitting light in a first range of wavelengths to the body proximate to the proximal end of the body; coupling a mirror to the body proximate to the distal end of the body; coupling a hot mirror to the body proximate to the proximal end of the body, wherein the hot mirror is capable of reflecting light in a second range of wavelengths and allowing light in the first range of wavelengths to pass through the hot mirror; coupling a first imaging system to the body proximate to the proximal end of the body, wherein the first imaging system is capable of creating a first image of a target area using light in the first range of wavelengths; coupling a second imaging system to the body proximate to the proximal end of the body, wherein the second imaging system is capable of creating a second image of the target area using light in the second range of wavelengths; wherein: the mirror is capable of reflecting light received by the mirror from the light source towards the target area, the mirror is capable of receiving a first portion of light in the first range of wavelengths reflected by the target area and a second portion of light in the second range of wavelengths emitted by the target area and directing the first portion of light and the second portion of light towards the proximal end of the body, the hot mirror is capable of transmitting at least a part of the first portion of light towards the first imaging system and reflecting at least a part of the second portion of light towards the second imaging system. In some aspects, the hot mirror can be replaced by a "cold mirror" capable of transmitting at least a part of the second portion of light towards the second imaging system and reflecting at least a part of the first portion of light towards the first imaging system.

In another aspect, the present patent document provides a method of thermographic ENT imaging by using a thermal imaging system which comprises an endoscope and a thermal imaging camera.

In another aspect, the present patent document provides a method of diagnosing or treating ENT conditions by performing thermographic ENT imaging using a thermal imaging system that comprises an endoscope and a thermal imaging camera, obtaining imaging data, and processing said data to produce a quantitative diagnostic metric.

DETAILED DESCRIPTION

At ENT clinics, otolaryngologists need to examine patients who report discomfort in the ear, nose, or throat areas. For the mouth and throat, a typical outpatient procedure is endoscopic imaging, which uses either a flexible or rigid endoscope in various forms to access the mouth and/or throat and relay a visible image to the operator's field of view through an eyepiece and/or an integrated camera. The trained clinician can then inspect the image to detect physiological abnormalities and check the muscle or tissue function.

Currently, endoscopes acquire images using visible-range or "white" light, which crucially (1) requires an integrated light source (e.g., LED, arc lamp, halogen lamp, laser) to illuminate a field of view and (2) delivers image contrast in the visible spectral range to which human eyesight is naturally sensitive.

There is some variation in this approach, such as using narrowband filters or light sources or imaging in the near-infrared. These alternatives can provide enhanced contrast to features such as vasculature. Because external illumination is required, image artifacts such as glare from the lamp are prominent due to the mucosal surface on a target area. Moreover, it is difficult or not possible to detect many subsurface features or conditions using imaging in the visible part of the spectrum only. Detecting subsurface features and/or conditions using images in the visible part of the spectrum only requires a degree of trained interpretation, and the patient health assessment is highly dependent on the clinician's experience.

Accordingly, there is a need for a device that can be used in the clinic to improve diagnostic confidence, without physicians having to resort to expensive imaging studies and/or prescribe unnecessary treatments. Subdermal contrast has previously been achieved using thermal cameras, particularly in the area of breast cancer. Recently, the cost and size of thermal cameras have become small enough to be useful in oral and nasal endoscopy.

Figure 1:
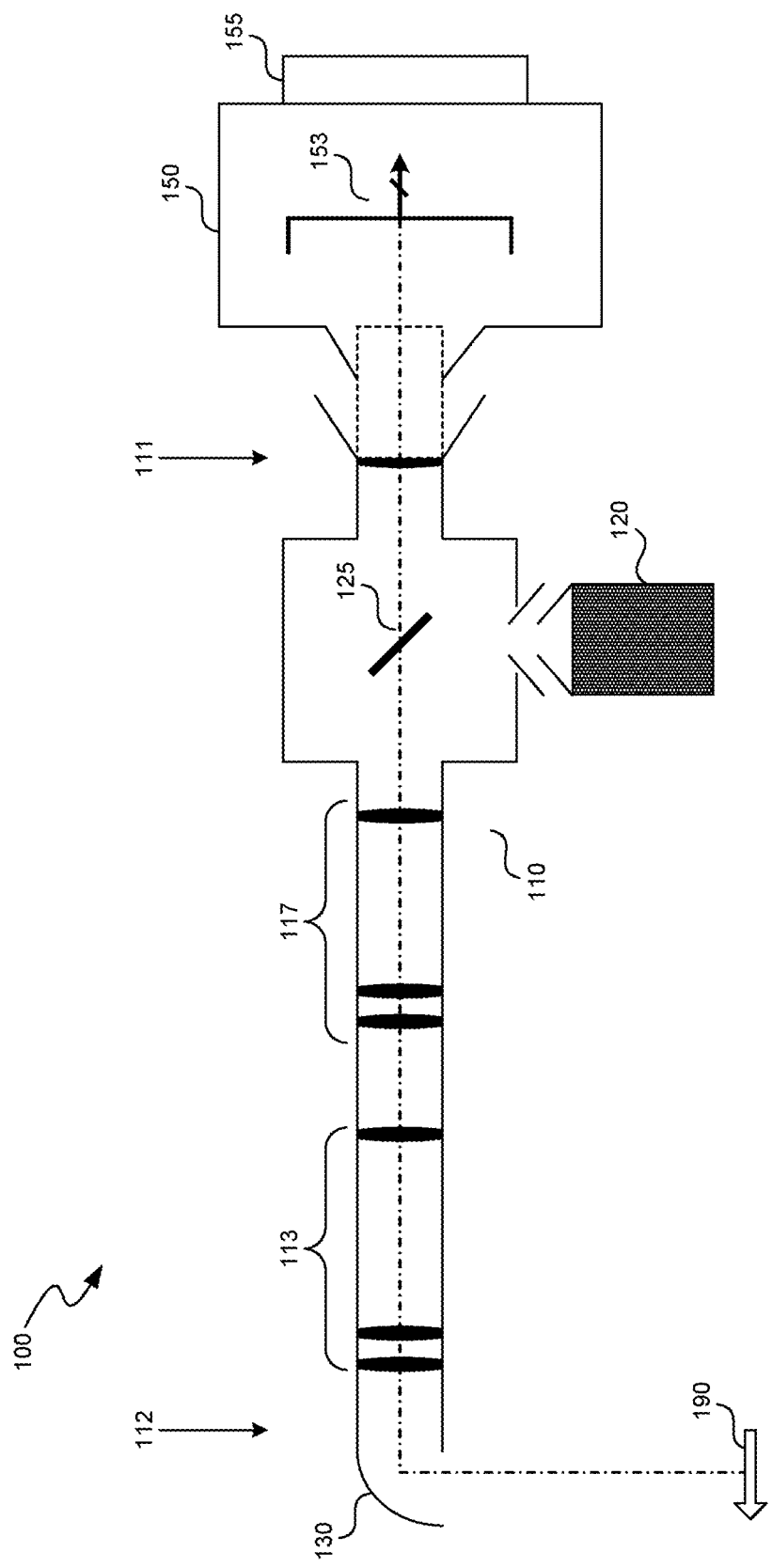
FIG. 1 shows a schematic of an endoscope incorporating a visible-range camera.

FIG. 1 is a schematic of a rigid endoscope 100 for imaging in a visible spectral range (a visible-range endoscope). Imaging target area 190 is, for example, inner throat of a patient. The endoscope 100 has a body 110 having a proximal end 111 and a distal end 112. The endoscope 100 directs light from a light source 120 to the target area 190 and collects light reflected from the target area 190. The light source 120 emits light in a visible spectral range (e.g., a range of wavelengths between 380 nm and 740 nm) and is attached to the body 110 at a location proximate to the proximal end of the body 110. Light in the visible spectral range can be directly perceived by a typical human eye.

To image features of the throat, the endoscope 100 is passed through the patient's mouth, and a mirror 130 both delivers light to the target area 190 and collects light reflected from the target area 190. The mirror 130 is attached to the body 110 proximate to the distal end of the body 110. The mirror 130 can be pivotably attached to the body 110. The mirror 130 can be removably attached to the body 110.

To deliver light from the light source 120 to the mirror 130, a beam splitter 125 located in the body 110 of the endoscope 100 can be used, for example. The beam splitter 125 reflects part of the light from the light source 120 towards the mirror 130 while another part of the light from the light source 120 passes through the beam splitter 125. In other implementations, one or more optical fibers can be used to deliver light from the light source 120 to the mirror 130 and/or to the target area 190 directly. Such optical fibers can be at least partially enclosed by the body 110.

Optical elements (e.g., single lenses or sets of several lenses) 113 and 117 housed in the body 110 of the endoscope 100 relay and magnify an image of the target area (e.g., the throat) onto an intermediate imaging plane which can be reimaged, for example, by an eyepiece for direct viewing by clinicians or by a camera 150 capable of capturing images in a visible spectral range ("visible-range camera"). For example, camera 150 can be connected to the body 110 proximate to the proximal end of the body 110. Camera 150 can include a sensor 153 to perform image capture. Sensor 153 can be of any type. For example, sensor 153 can be a charge-coupled device (CCD) or a CMOS (complementary metal-oxide-semiconductor)-based sensor. Images captured by the camera 150 can be read out to a computer (not shown) using an analog-to-digital converter (ADC) and/or readout integrated circuit (ROIC) 155 via a wired or wireless interface (e.g., USB, Ethernet, Wi-Fi, or Bluetooth) embedded into the camera 150 or housed in the body 110 of the endoscope 100 or connected to the body 110 of the endoscope 100.

Figure 2:
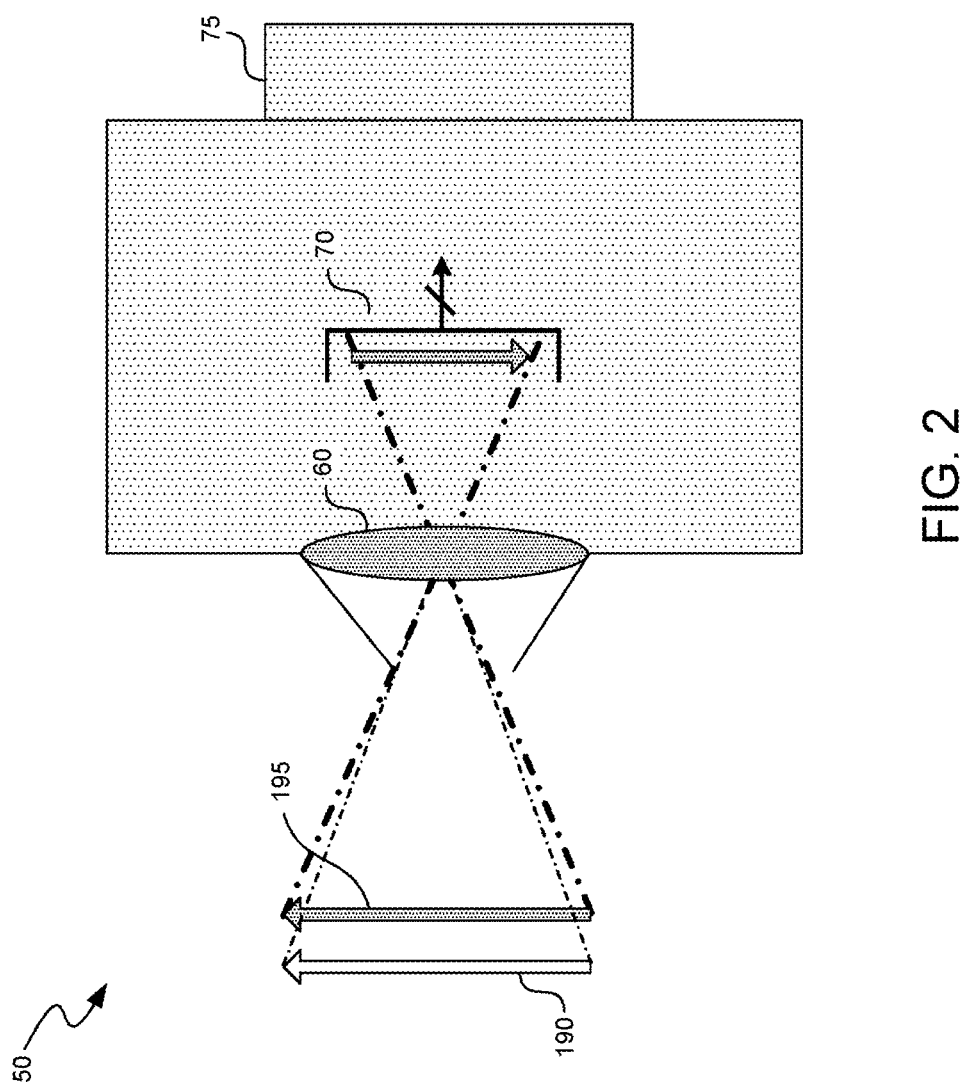
FIG. 2 shows a schematic of a thermal camera imaging system.

FIG. 2 is a schematic of a camera imaging system 50 capable of capturing images in a thermal spectral range ("thermal-range camera" or "thermal camera"). Objects with a defined temperature emit light, whose spectrum depends on the particular temperature. Increases in temperature result in a shift of this radiation spectrum and an increase in the total amount of radiated energy, according, for example, to the formulas describing blackbody radiation. For terrestrial objects at ambient temperature, this spectrum is predominantly invisible and typically falls in the 8-14 micrometer band, which is termed the thermal infrared band. As objects get hotter, the amount of radiation in the thermal infrared band increases, while cooling objects will emit less radiation in the same band.

Materials that are sensitive to this thermal radiation can be calibrated to measure the temperature of objects based on the amount of received radiative power and, when defined in size and arranged into a grid, are referred to as focal plane arrays (FPA). FPA sensors can be paired, for example, with a thermal infrared transmissive lens, e.g. lens 60 in FIG. 2, to form a thermal camera 50 that images thermal radiation from objects (e.g., thermal radiation 195 from a target area 190 in FIG. 2) onto the FPA (e.g., FPA 70 in FIG. 2). FPA 70 of the camera 50 can be, for example, an uncooled bolometer focal plane array. Images captured by the thermal camera 50 can be read out to a computer (not shown) using an analog-to-digital converter and/or readout integrated circuit 75 via a wired or wireless interface (e.g., USB, Ethernet, Wi-Fi, or Bluetooth) embedded into the camera 50 and/or connected to the camera 50. In some embodiments, the computer can be embedded into the camera 50.

Lens 60 of the thermal camera 50 can be made using, for example, the following materials which are transmissive to both visible-range and thermal-range radiation: potassium bromide, sodium chloride, zinc sulfide, zinc selenide. Or, as shown in FIG. 2, lens 60 can be made using materials which are opaque to visible-range light but transparent (to one degree or another) to thermal-range radiation such as, for example, silicon or germanium.

A figure of merit of a thermal-range camera can be specified, for example, by its noise equivalent temperature difference (NETD), which is defined as the temperature difference between two points of an object that is equivalent to the noise level temperature variance in the FPA readout.

While thermal camera systems have remained traditionally bulky, power-hungry, and expensive due to the cooling units required to reduce NETD to a useable level (particularly for bandgap sensors such as HgCdTe), recent advances in uncooled microbolometers have allowed to produce thermal cameras which have NETD comparable to that of older thermal cameras yet have form factors similar to those of visible-range cameras and cost a fraction of the price of the older thermal cameras.

During processing of the acquired thermal images, scores can be assigned to the thermal images by examining a likelihood that a rise in temperature or lack thereof in a certain area of interest in the images is significant. To calculate this likelihood, factors to consider can include, for example, temperatures of the surrounding areas, temperature readings from one or more earlier time-points, and temperature readings with reference to a standard temperature in the body. Temperature dynamics and spatial averaging can also be used to provide additional data points to be correlated with specific conditions. Physicians can use the quantitative score information to make more informed decisions.

The obtained information (e.g., temperature of the area of interest and/or that of surrounding areas and/or calculated score values) can be overlaid on the thermal video. Presentation (e.g., visualization) of the thermal data can be provided using single and/or multiple metrics, such as, for example, 2D temperature/scoring maps, 1D temperature time histories, histograms, and various statistical metrics. Clinicians can also build a database for each patient to monitor the progress of the patient's condition or therapy.

Figure 3:
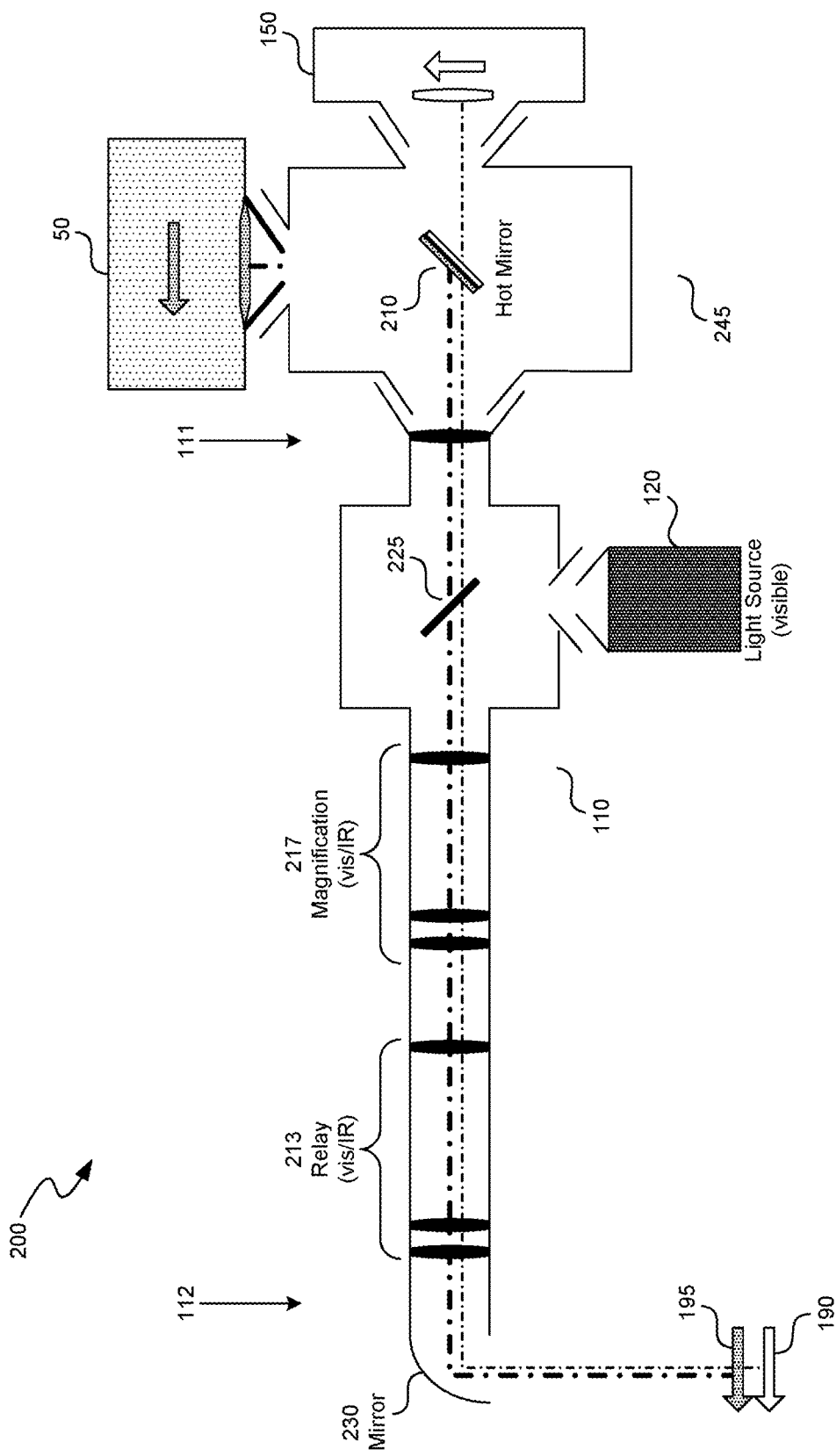
FIG. 3 shows a schematic of an endoscope which incorporates both a visible-range camera and a thermal-range camera and in which the thermal-range and the visible-range optical paths are integrated.

FIG. 3 shows an endoscope 200 according to an embodiment of the technology disclosed in this patent document that integrates a thermal infrared and a visible spectrum optical paths within a body 110 having a proximal end 111 and a distal end 112. As shown in FIG. 3, the target area 190 is imaged both in a visible spectral range and a thermal spectral range. During thermal imaging, thermal radiation 195 emitted by the target area 190 is registered by the endoscope 200.

In endoscope 200, the visible camera attachment 150 which is traditionally attached to an eyepiece of an endoscope (e.g., endoscope 100) is replaced with an attachment 245 connected to the body 110 proximate to its proximal end. The attachment 245 houses both a visible-range camera 150 and a thermal-range camera 50. A "hot mirror" 210 located inside the attachment 245 is configured to reflect thermal radiation into the thermal-range camera 50 and pass visible light into the visible-range camera 150.

Optical materials of the endoscope 200 are transmissive to both thermal infrared light and visible light, which can be implemented using materials such as ZnSe. Since both thermal and visible optical paths are relayed through the same optical elements of the endoscope 200 (e.g., lenses or lens sets 213 and 217, mirror 230, beam splitter 225), the optical elements of the endoscope 200 should preferably minimize aberrations in both thermal infrared and visible spectral ranges.

Beam splitter 225 of the endoscope 200 reflects part of the light produced by the light source 120 attached to the body 110 proximate to its proximal end towards the mirror 230 which is attached to the body 110 proximate to its distal end and which directs the light received from the light source 120 towards the target area 190. The light source 120 emits light in a visible spectral range (e.g., a range of wavelengths between 380 nm and 740 nm or one or more wavelengths in any of the following ranges: 380-450 nm, 450-485 nm, 485-500 nm, 500-565 nm, 565-590 nm, 590-625 nm, or 625-740 nm). As with the endoscope 100, various ways of delivering light from the light source 120 to the mirror 230 and/or directly to the target area 190 can be used. For example, the light can be delivered using an optical fiber or several optical fibers instead of or in addition to using the beam splitter 225.

Mirror 230 receives light in the visible spectral range reflected by the target area 190 as well as light in a thermal infrared spectral range (e.g., a range of wavelengths between 8 µm and 14 µm) emitted by the target area and directs the light received from the target area to the optical elements housed inside the body 110 of the endoscope 200. Optical elements 213 and 217 (each of which can be a single lens or a set of several lenses) relay and/or magnify a visible-range image of the target area (e.g., throat of a person) as well as a thermal image of the target area. The radiation (both visible and thermal infrared) from the target area 190 passes through the beam splitter 225 after which thermal part of the radiation is directed by the "hot mirror" 210 into the thermal-range camera 50 while the visible part of the radiation passes through the mirror 210 into the visible-range camera 150. The thermal-range camera 50 and the visible-range camera 150 obtain a thermal image of the target area and a visible-range image of the target are, respectively.

Figure 4:
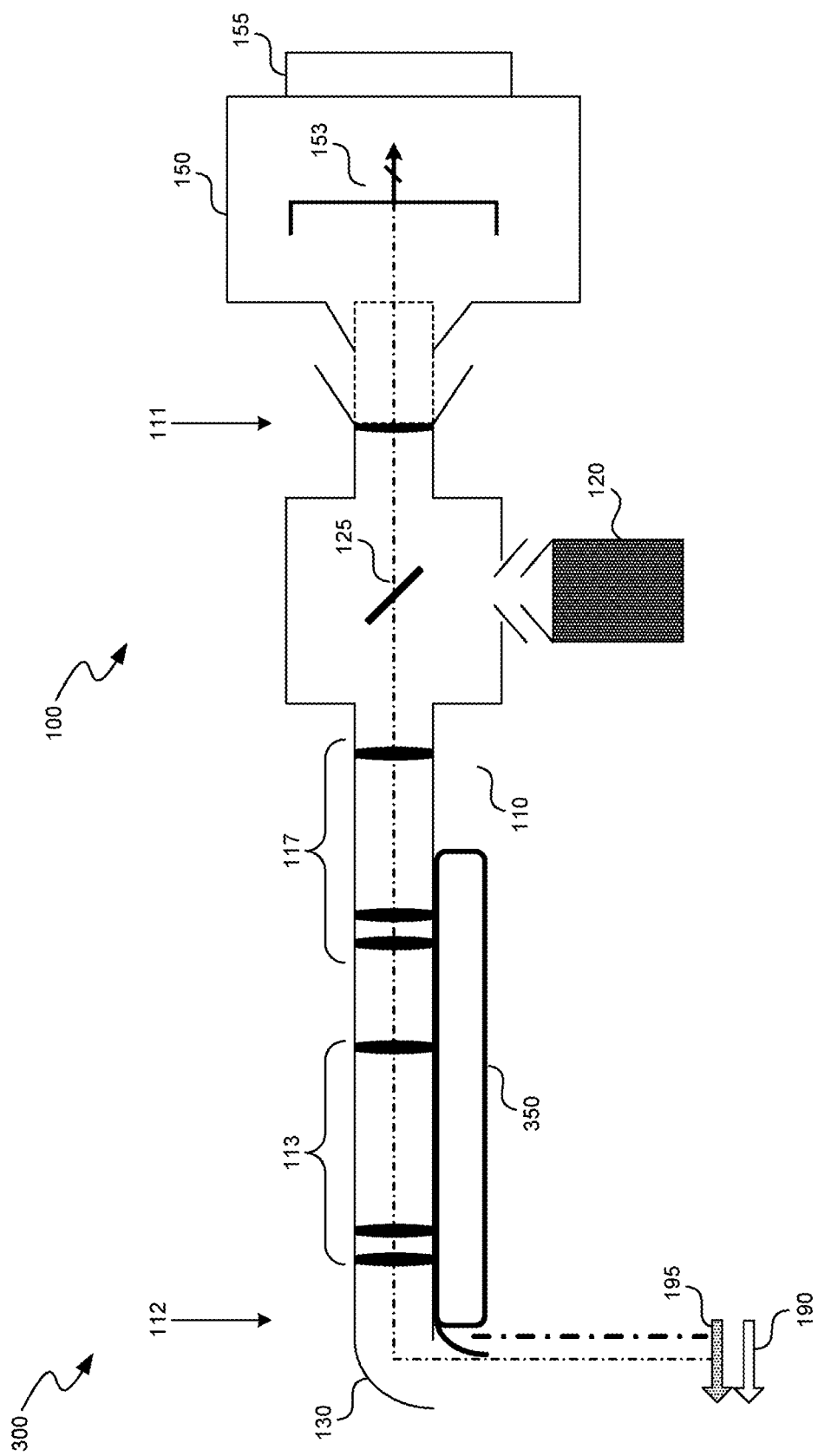
FIG. 4 shows a schematic of an endoscope which incorporates both a visible-range camera and a thermal-range camera and in which the thermal-range and the visible-range optical paths are separated.

FIG. 4 shows an example of an endoscope 300 according to an embodiment of the technology disclosed in this patent document. Endoscope 300 separates a thermal infrared and a visible spectrum optical paths. Endoscope 300 comprises an endoscope 100 which performs imaging of the target area 190 in a visible spectral range (e.g., a range between 380 nm and 740 nm) and a thermal imager 350 attached to the endoscope 100 which is used to perform imaging of the target area in a thermal infrared spectral range (e.g., a range between 8 µm and 14 µm).

Figure 5:
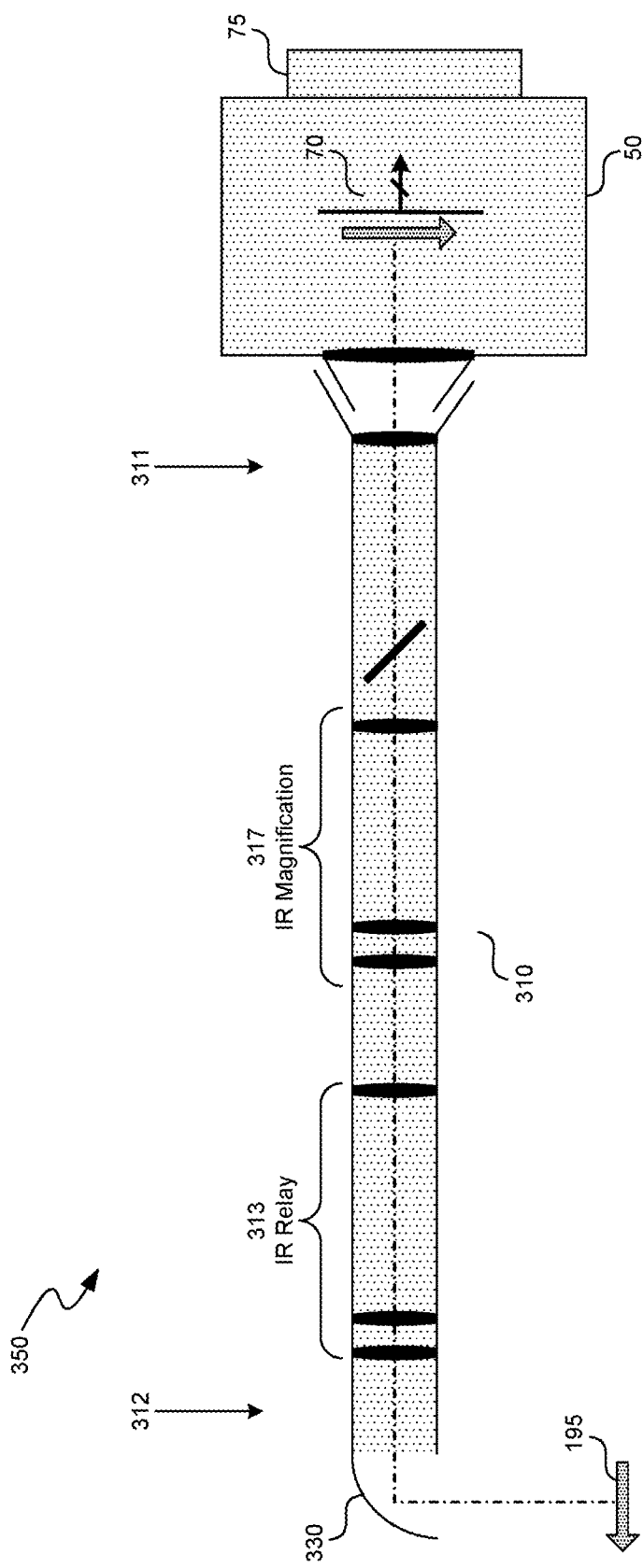
FIG. 5 shows a schematic of a thermal imager of the endoscope shown in FIG. 4.

As shown in FIG. 5, in some embodiments, the thermal imager attachment 350 comprises a body 310 having a proximal end 311 and a distal end 312, and an optical system which incorporates a viewing mirror 330 attached to the body 310 at its distal end, relay and/or magnification optical systems 313 and 317 housed in the body 310, as well as a thermal camera 50 attached to the body 310 proximate to its proximal end. The mirror 330 can be pivotably attached to the body 310. The mirror 330 can be removably attached to the body 310. Thermal radiation 195 emitted by the target area 190 is directed by the mirror 330 into the optical systems 313 and 317 which transmit it to the thermal-range camera 50 which captures an image of the target area in a thermal spectral range. Images captured by the visible-range camera 150 of an endoscope (e.g., endoscope 100) to which the thermal imager 350 is attached and images captured by the thermal-range camera 50 of the thermal imager 350 can be transmitted to, for example, a computer (not shown) or another electronic device which can process the images. Image transmission can be performed via a wired (e.g., USB, Ethernet) or a wireless interface (e.g., Wi-Fi, Bluetooth). The interface can be incorporated into any of the thermal imager 350, thermal-range camera 50, visible-range camera 150 or the endoscope (e.g., endoscope 100), for example. The computer or another electronic device can be embedded into the thermal imager 350, for example.

Optical materials used in the thermal imager 350 can be selected or designed for optimal transmission and imaging in a thermal infrared spectral range (e.g., a range of wavelength from the range between 8 µm and 14 µm) to minimize both intensity loss and aberrations in the thermal infrared spectral range. The thermal imager 350 can be used as an attachment to a visible-range endoscope (e.g., endoscope 100) and, in some embodiments of the technology disclosed in this patent document, the thermal imager 350 can also be used by itself for thermographic-only endoscopy. If used as an attachment to an endoscope, the field of view of the endoscope and the field of view of the thermal imager 350 can be configured to overlap via mechanical alignment of the optical elements of the endoscope and/or the thermal imager 350 (e.g., mirror 130 and/or mirror 330) and/or through alignment of the visible-range and thermal-range images during processing of the captured visible-range and thermal-range images.

Figure 6:
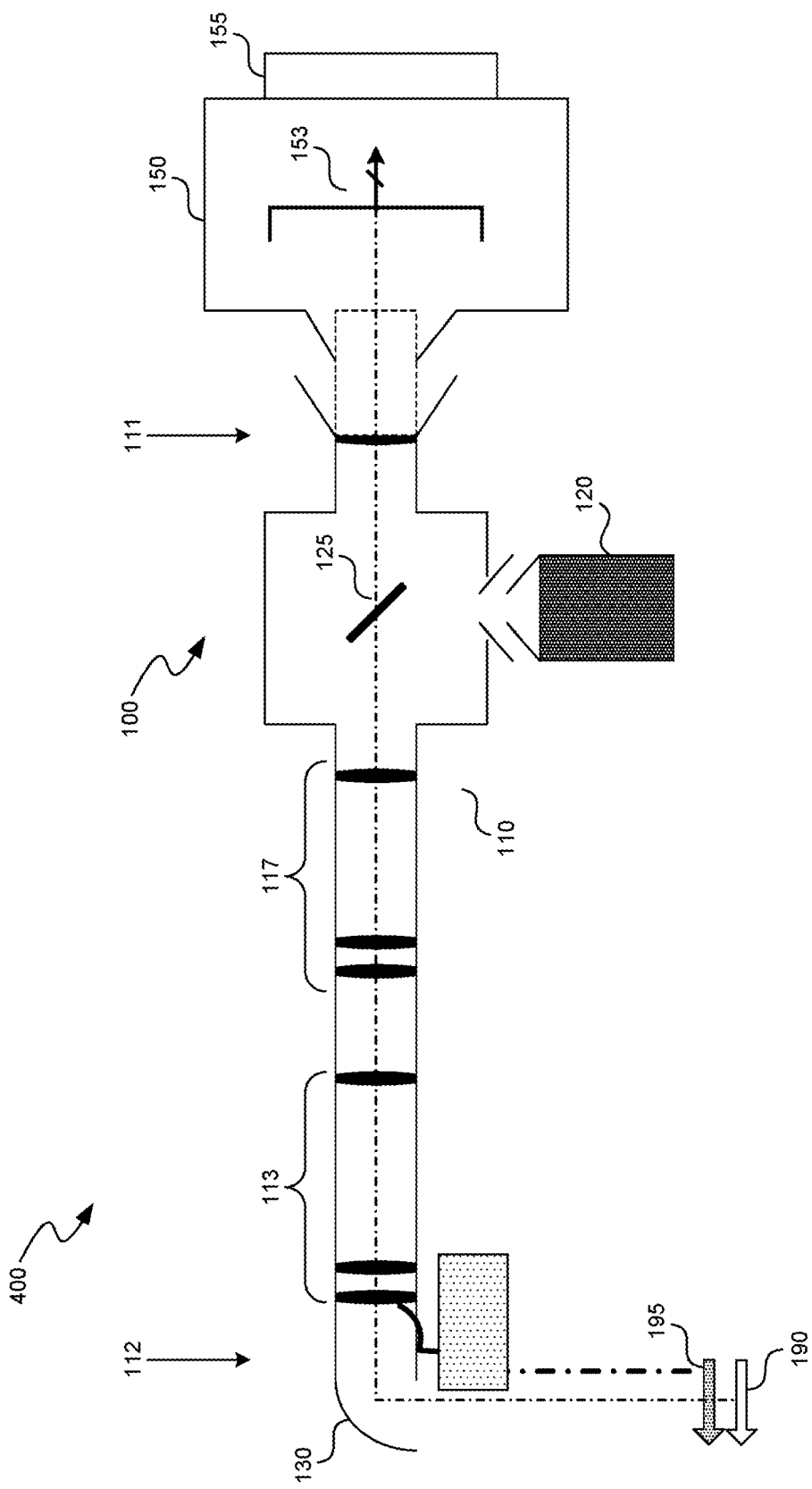
FIG. 6 shows a schematic of an endoscope which incorporates both a visible-range camera and a thermal-range camera.

FIG. 6 shows an endoscope 400 according to an embodiment of the technology disclosed in this patent document. The endoscope 400 comprises a thermal camera 50 attached to the distal end of the body 110 of the endoscope 400. The thermal camera 50 can incorporate an uncooled microbolometer focal plane array as its sensor, for example. Endoscope 400 also comprises a visible-range camera 150 and provides both thermal-range and visible-range images and/or video to a computer via a wired (e.g., USB or Ethernet) or wireless (e.g. Wi-Fi or Bluetooth) connection. The communication hardware can be embedded into one or both cameras of the endoscope 400 and/or housed in or attached to the body 110 of the endoscope 400. Power for operation of the cameras and other electronics of the endoscope 400 can be provided via an external power source or via a battery (rechargeable or otherwise) housed in the body 110 of the endoscope 400 or attached to the endoscope 400. Other embodiments of the technology disclosed in this patent document (e.g., endoscopes 200, 300, 500) can also be provided with wired or wireless communication means (e.g., USB, Ethernet, Wi-Fi, or Bluetooth interfaces) as well as means to provide power to the cameras and electronics of the embodiments from an external and/or an internal power source (e.g., a battery and/or a power connector).

Figure 7:
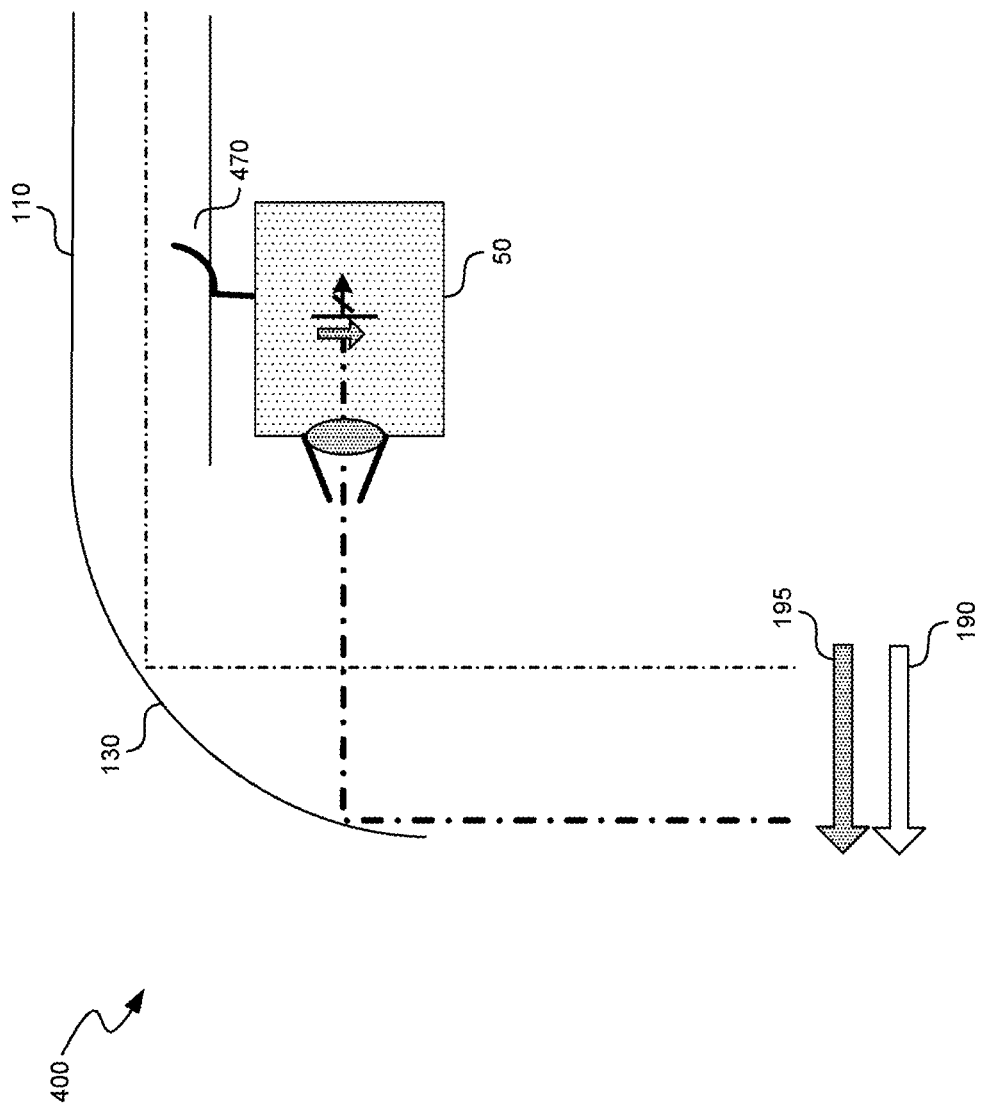
FIG. 7 illustrates an embodiment of the endoscope shown in FIG. 6.

FIG. 7 shows an indirect-viewing configuration of the endoscope 400. The thermal camera 50 is facing a viewing mirror 130 which can be pivotably connected to the body 110 of the endoscope 400, for example. A variety of attachment means 470 can be used to attach the camera 50 to the body 110 in this and other configurations of the endoscope 400. For example, a bracket, a strap, or a clamp can be used for that purpose. Thermal infrared light 195 emitted by the target area 190 is directed by the mirror 130 into the thermal camera 50 while visible-range light reflected by the target area is directed by the mirror 130 into the body 110 of the endoscope 400.

Figure 8:
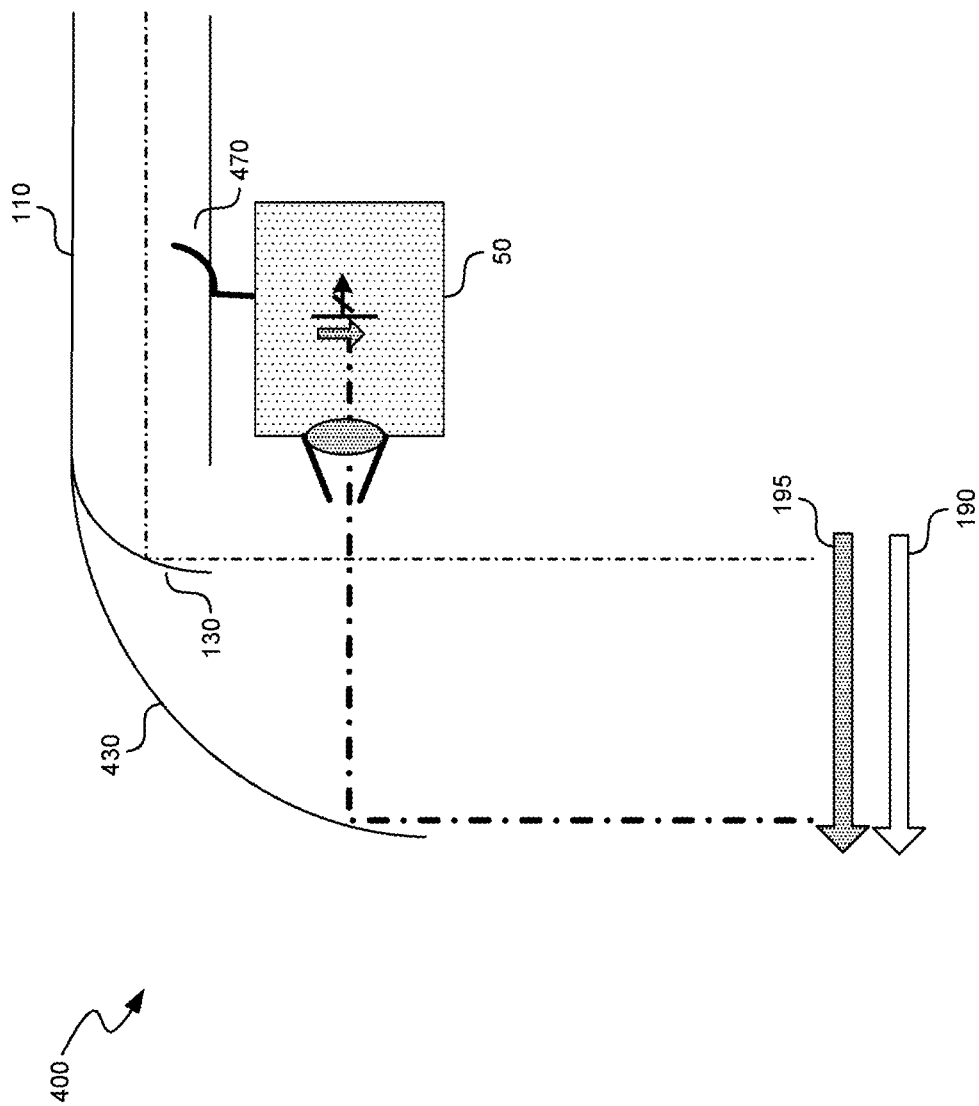
FIG. 8 illustrates another embodiment of the endoscope shown in FIG. 6.

FIG. 8 shows another implementation of the indirect-viewing configuration of the endoscope 400. In the implementation shown in FIG. 8, mirror 430 is attached to the body 110 of the endoscope 400 in addition to the mirror 130. Any of the mirrors 130 or 430 can be fixedly or pivotably attached to the body 110. Mirror 130 directs light in a visible spectral range reflected by the target area 190 into the body 110 of the endoscope 400 while mirror 430 directs thermal radiation 195 emitted by the target area into the thermal camera 50.

Figure 9:
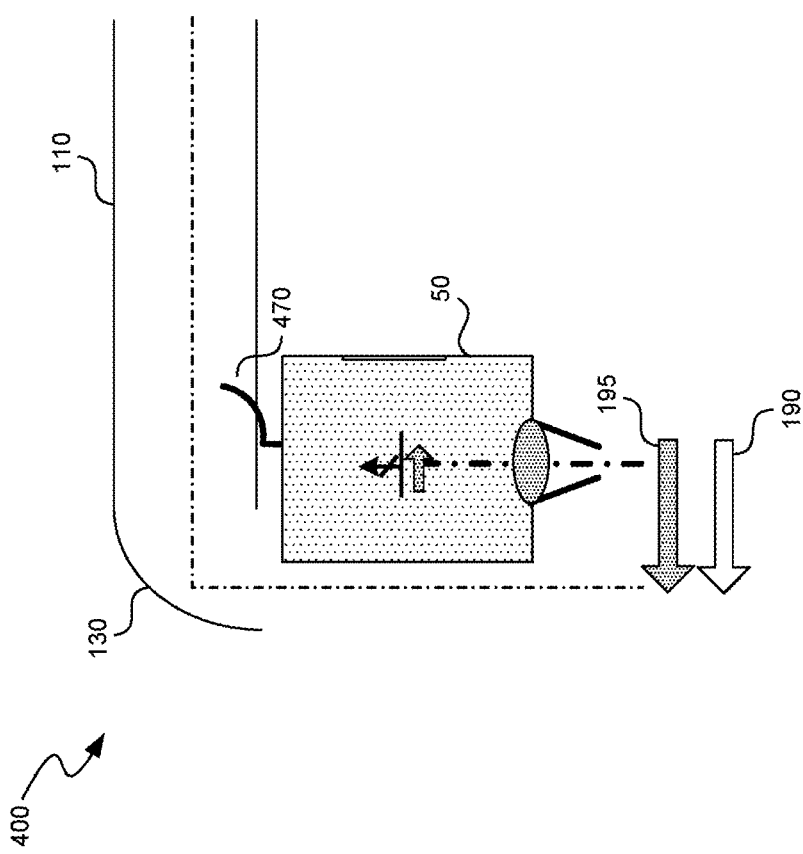
FIG. 9 illustrates yet another embodiment of the endoscope shown in FIG. 6.

FIG. 9 shows a direct-viewing configuration of the endoscope 400. In this configuration, thermal camera 50 is facing the target area 190 (e.g., patient's throat) directly. A thermal image is directly formed from the thermal infrared light 195 emitted by the target area, without reflection from an intermediate mirror.

Figure 10:
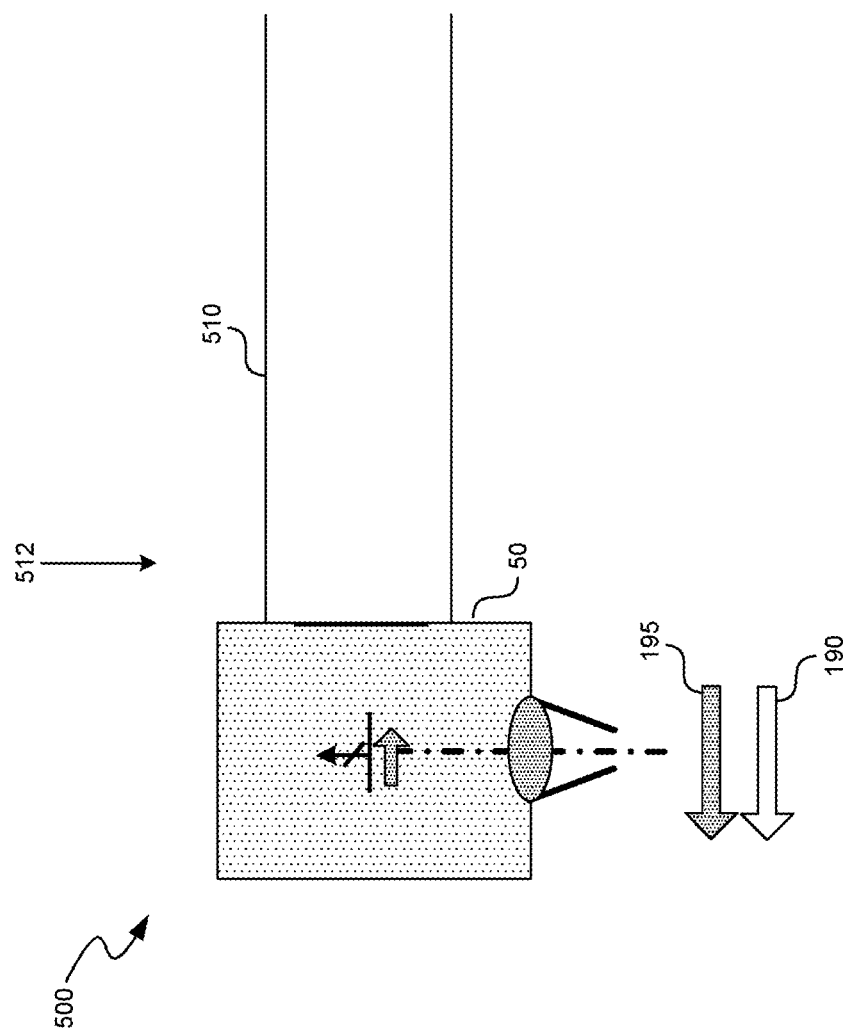
FIG. 10 shows a schematic of an endoscope which incorporates a thermal-range camera.

FIG. 10 shows an endoscope 500 according to an embodiment of the technology disclosed in this patent document. A rigid body 510 of the endoscope 500 has a small thermal camera unit 50 attached to its distal end 512 and facing a target area (e.g., the throat of a patient).

To minimize profile and complexity of the endoscope 500, it does not perform simultaneous visible-range imaging of the target area and body 510 of the endoscope 500 has no internal optics, save for possible electronics cabling (e.g., serial, USB3, or Ethernet) used to transfer images from the thermal camera 50 to a computer. Camera 50 or body 510 of the endoscope 500 can also incorporate a Wi-Fi module or a Bluetooth module for wireless transfer of the captured thermal images or video to a computer. In some embodiments, the computer is incorporated into the body 510 of the endoscope 500. The body 510 can also incorporate a battery or several batteries (rechargeable or otherwise) to provide power to the electronic elements of the endoscope 500 such as its camera 50 or elements of the communication electronics (e.g., the Wi-Fi module). Alternatively, an external power source can be used to provide power to the endoscope 500. Such a power source can be connected to the endoscope 500 via a micro-USB port or a power connector, for example.

Figure 11:
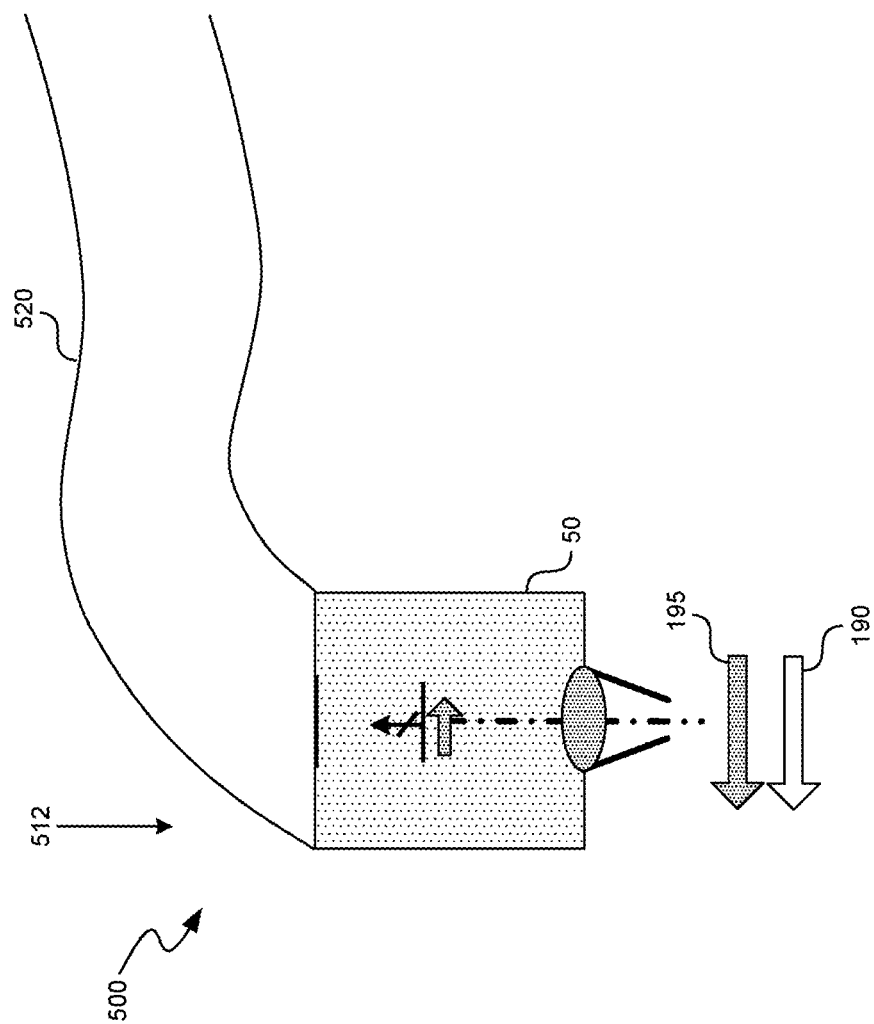
FIG. 11 illustrates an embodiment of the endoscope shown in FIG. 10.

FIG. 11 shows a configuration of the endoscope 500 in which the rigid body 510 is replaced by a flexible and/or bendable body 520. Hand-operated actuators similar to those in existing flexible endoscopes can be used to maneuver and manipulate thermal camera 50 in rotation and position.

Figure 12:
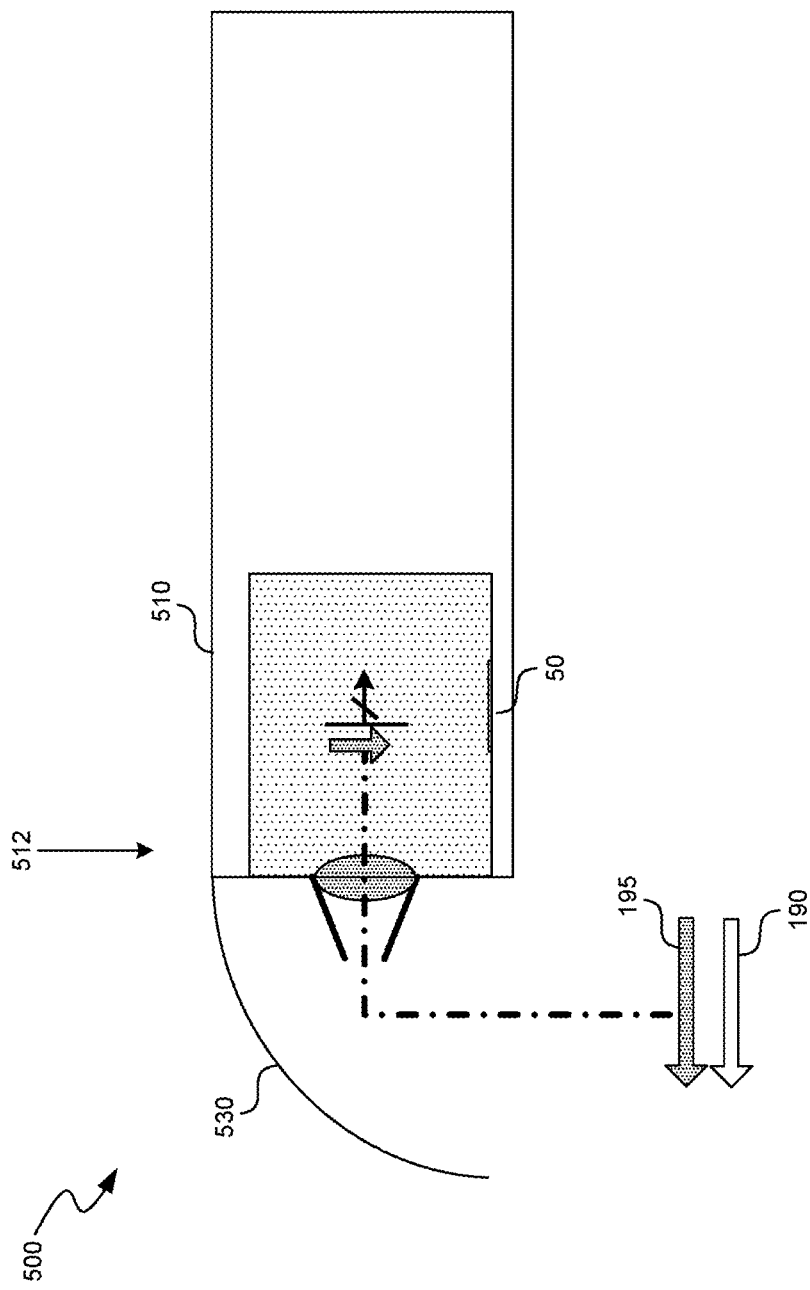
FIG. 12 illustrates another embodiment of the endoscope shown in FIG. 10.

FIG. 12 shows an implementation of the endoscope 500 in which thermal camera 50 is located proximate to the distal end 512 of the endoscope body 510 and is at least in part enclosed by the body 510. The implementation of the endoscope 500 shown in FIG. 12 includes a mirror 530 attached to the distal end of the body 510 and configured to direct thermal radiation 195 emitted by the area of interest 190 into the camera 50. Endoscope body 510 can include cabling to provide image transfer from the camera 50 to a computer as well as to control the camera 50 via, for example, a USB or a serial interface; it can also include cables providing power to the camera 50; body 510 can also incorporate a power source in a form of a rechargeable battery, for example, as well as a connector (e.g., a micro-USB one) to supply power from an external power source to the endoscope 500 and/or to the rechargeable battery; body 510 of the endoscope 500 can also house one or more communication modules such as a Wi-Fi or a Bluetooth one to provide wireless transfer of the images captured by the camera 50 to a (remote) computer and/or to control the camera operation.

Figure 13:
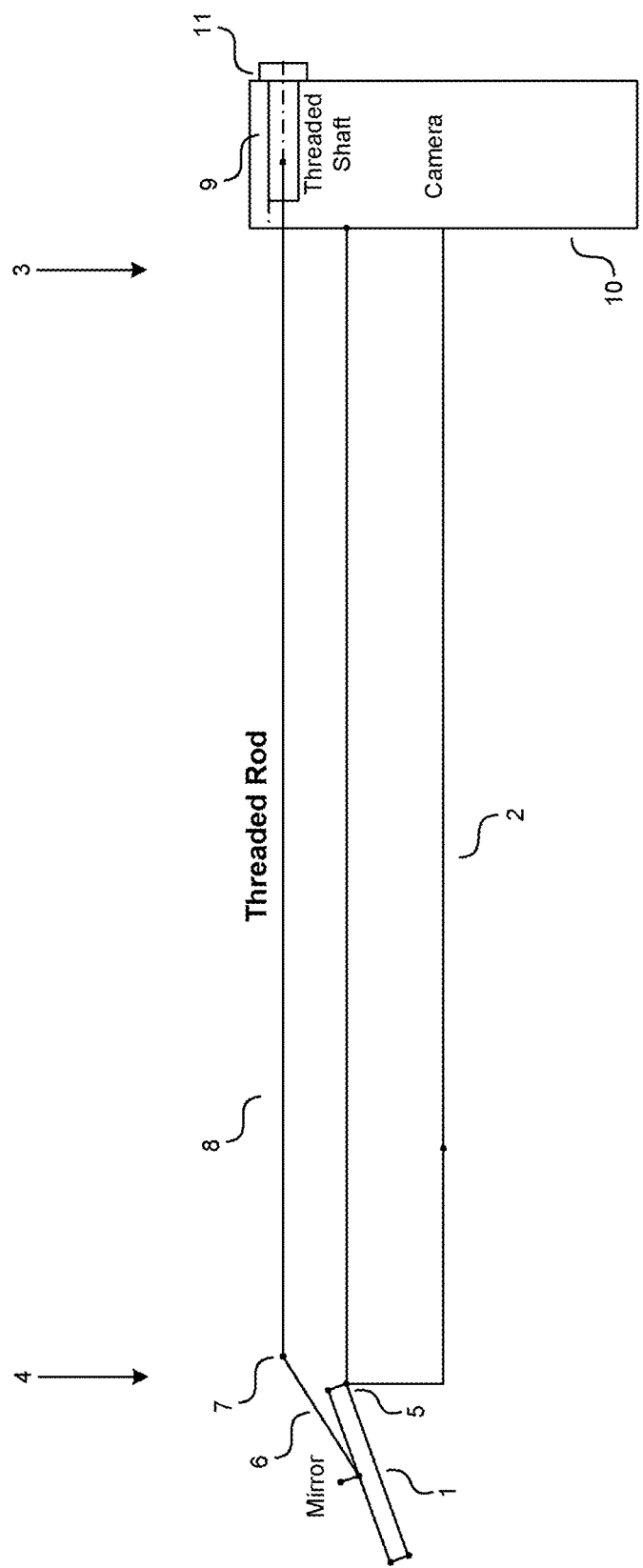
FIG. 13 shows a schematic of an endoscope which incorporates a mechanism for adjusting tilt of a mirror.
Figure 14:
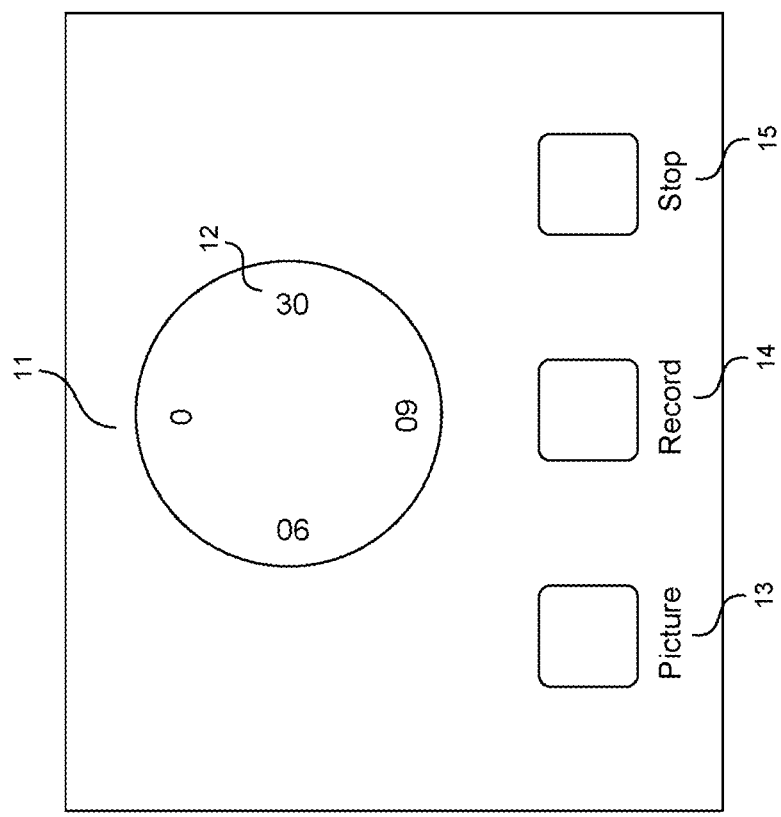
FIG. 14 shows a schematic of an interface which can be used to adjust tilt of the mirror.

As described above, some embodiments of the technology disclosed in this patent document include a mirror which is typically attached to a distal end of an endoscope (other points of the mirror attachment are possible as well) and which is configured to direct at least one of visible-range light or thermal-range light received by the mirror from a target area to the elements of the endoscope (e.g., lenses and/or or a camera). As shown in FIG. 13, such a mirror 1 used in an embodiment of an endoscope according to the technology disclosed herein can be attached to the body 2 of the endoscope at a distal end 4 of the body using a hinge 5 connected to the body and allowing the mirror to be tilted at different angles in a plane containing an axis connecting a proximal end 3 and the distal end 4 of the endoscope body 2. A thin metal rod 6 can be attached between the mirror 1 and another hinge connection 7 which connects the rod 6 and a threaded rod 8. The threaded rod 8 is inserted into a threaded shaft 9 which allows the threaded rod 8 to move in and out of the shaft. The threaded shaft 9 can be positioned, for example, proximate to a camera 10 (e.g., an infrared one) of the endoscope. Moving the rod 8 back and forth in the shaft 9 will cause the mirror to tilt up and down along a direction which is perpendicular to the axis connecting the distal and proximal ends 4 and 3 of the endoscope body 2. The mirror can generally rotate between 0 degrees and 90 degrees relative to the axis connecting the distal and proximal ends 4 and 3 of the endoscope body 2. The length of the rod 8 protruding from the shaft 9 can be controlled by a knob 11 that is labelled with mirror tilt angle measurements, as shown in FIG. 14. The knob 11 can connect, for example, to gears within the endoscope that adjust the position of the threaded rod 8 within the threaded shaft 9.

In some implementations, rod 6, threaded rod 8 and/or threaded shaft 9 can be positioned inside the endoscope body 2. Mechanisms other than the example one described above can be used for adjusting a tilt and/or a position and/or orientation of a mirror of an endoscope or that of a camera of the endoscope relative to a body of the endoscope according to the technology disclosed herein.

FIG. 14 shows an example of a proximal-end user control interface of an endoscope according to an embodiment of the technology disclosed herein. In the example design shown in FIG. 14, the knob 11 is used for mirror tilt adjustment and three buttons (13 "Picture", 14 "Record", and 15 "Stop") function to control one camera (e.g. the thermal one of the embodiment 500 described above) or both cameras (the thermal one and the visible-range one included in the embodiments 200, 300, or 400 described above) of the endoscope. Markings 12 shown on the knob 11 (e.g., "0", "30", "60", "90" as shown in FIG. 14) correspond to the tilt angle of the mirror 1 of the endoscope, as described above. In response to a user pressing the button 13 ("Picture"), each camera of the endoscope can take a single picture of a target area and transfer it to a (remote) computer. In response to the user pressing the button 14 ("Record"), each camera of the endoscope can start taking a video of the target area and transferring it to a (remote) computer until the user presses the button 15 ("Stop").

The mirror tilting means and/or the proximal-end user control interface described above can be incorporated into any embodiment of the endoscope according to the technology disclosed herein.

Figure 15:
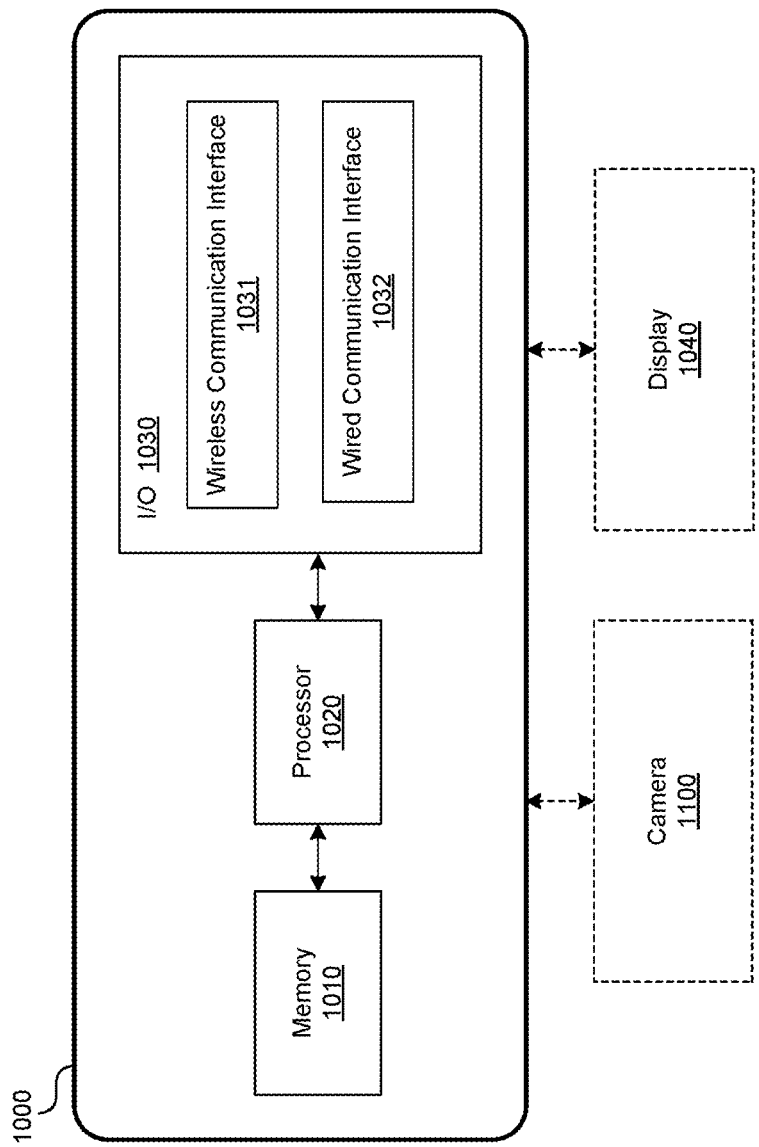
FIG. 15 shows a schematic of a data processor which can interface with various elements of various embodiments of an endoscope according to the technology disclosed in this patent application.

FIG. 15 shows a block diagram of an example embodiment of an electronic device (data processor) 1000 which can interface with various elements of various embodiments of an endoscope according to the technology disclosed in this patent application which will be referred to as endoscope 2000 below.

In some embodiments, data processor 1000 can include a processor 1020 to process data, a memory 1010 in communication with the processor 1020 to store data, and an input/output (I/O) communication interface 1030 to interface the processor 1020 and/or the memory 1010 to other elements of the endoscope 2000 as well as to various modules, units, or devices, including external computing devices, data storage devices, or communication devices, for example.

For example, the processor 1020 can include a central processing unit (CPU) or a microcontroller unit (MCU) or a graphics processing unit (GPU). For example, the memory 1010 can include and store processor-executable code, which, when executed by the processor 1020, configures the data processor 1000 to perform various operations, e.g., such as receiving information, commands, and/or data, processing information, commands, and/or data, and transmitting or providing information, commands, and/or data to another element of the endoscope 2000 and/or to other devices external to the endoscope 2000.

In some implementations, the data processor 1000 can transmit raw or processed data (e.g., images captured by a visible-range camera or a thermal-range camera of the endoscope 2000) to a computer system or a computer network which can be accessible via a communication network such as the Internet (such computer systems or networks are sometimes referred to as being located 'in the cloud') that includes one or more remote computational processing devices (e.g., servers).

To support various functions of the data processor 1000, the memory 1010 can store information and data, such as instructions, software, values, images, and other data processed or referenced by the processor 1020. For example, various types of Random-Access Memory (RAM) devices, Read Only Memory (ROM) devices, Flash Memory devices, and other suitable storage media can be used to implement storage functions of the memory 1010.

The I/O 1030 can include at least one of the wireless communication interface 1031 or wired communication interface 1032. The wireless communication interface 1031 can be a wireless transmitter to transmit stored and/or processed data, for example, or a wireless transceiver (Tx/Rx) to transmit and receive data, for example. The wired communication interface 1032 can be a wired transmitter to transmit stored and/or processed data, for example, or a wired transceiver (Tx/Rx) to transmit and receive data, for example.

The I/O 1030 of the data processor 1000 can utilize various types of wired interfaces 1032 or wireless interfaces 1031 compatible with typical data communication standards which can be used in communications of the data processor 1000 with other devices, e.g., including, but not limited to, Bluetooth, Bluetooth low energy, Zigbee, IEEE 802.11, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE/5G cellular communication methods, NFC (Near Field Communication), serial and parallel interfaces, USB, Ethernet.

In some embodiments, the data processor 1000 can include or be communicatively coupled to a display unit 1040, which can include a visual display such as a display screen, an audio display such as a speaker, or other type of a display or a combination thereof.

The I/O 1030 of the data processor 1000 can also interface with external interfaces, sources of data, data storage devices, and/or visual, audio, or haptic display and/or feedback devices, etc. to retrieve and transfer data and information, for example, which can be processed by the processor 1020, and/or stored in the memory 1010, and/or exhibited using an output unit (e.g., the display unit 1040).

For example, the display unit 1040 can be configured to be in data communication with the data processor 1000, e.g., via the I/O 1030 (FIG. 15), and to provide a visual display, or an audio display, and/or other sensory display of images, data and/or other information to a user. In some examples, the display unit 1040 can include various types of screen displays, speakers, or printing interfaces, e.g., including but not limited to, light emitting diode (LED), or liquid crystal display (LCD) monitor or screen, cathode ray tube (CRT) as a visual display; audio signal transducer apparatuses as an audio display; toner, liquid inkjet, solid ink, dye sublimation, inkless (e.g., such as thermal or UV) printing apparatuses, etc.

As shown in FIG. 15, in some embodiments, data processor 1000 can be communicatively coupled to a camera 1100 of the endoscope 2000 which can be a visible-range camera or a thermal-range camera. Data processor 1000 can also be communicatively coupled to more than one camera of the endoscope 2000. For example, the data processor 1000 can be communicatively coupled to both a visible-range camera and a thermal-range camera of the endoscope 2000.

In some embodiments, data processor 1000 can be included into a visible-range camera of the endoscope 2000. In some embodiments, data processor 1000 can be included into a thermal-range camera of the endoscope 2000. Some embodiments of an endoscope according to the technology disclosed herein involve both a visible-range camera and a thermal-range camera of the endoscope having a copy of the data processor 1000. In some embodiments, data processor 1000 can be housed in a body of the endoscope 2000.

In various implementations, the data processor 1000 can be operable to store and execute software applications and algorithms and implement various controls of an endoscope according to the technology disclosed in the present patent application.

Because thermal-range camera and visible-range camera of an endoscope according to some embodiments of the technology disclosed in this patent document can have different fields of view, the same features of an imaged target area can have different positions within a thermal-range image and a visible-range image acquired by the cameras. Image processing of the captured visible-range and thermal-range images can include a step of aligning corresponding features in these images. This step can compensate for misalignment of the cameras.

Transformation of one of the thermal-range image or visible-range image or both of those images which compensates for misalignments between them can be determined before conducting an endoscopic procedure. For example, the steps of determining properties (e.g., coefficients) of such a transformation can include steps of taking images of a checkerboard with black and white squares using both the thermal-range camera and the visible-range camera, manually clicking on four corners of a checkerboard square in an image produced by the visible-range camera and the corresponding four points in a thermal-range image, and estimating geometric transformation to map the four points from the visible-range image to the four points in the thermal-range image. Any image alignment method or procedure other than the one described above can be used for alignment of the thermal-range and visible-range images.

After the properties of the image transformation are established, it can be applied to visible-range images, for example, to align them with the corresponding thermal-range ones. As a result of this image alignment, every pixel location in the visible-range image will be mapped to a point or an area in a corresponding thermal-range image. After the thermal-range and the visible-range images are aligned, they can be displayed as overlaid one on top of another in software, for example. The software can allow a user to adjust a degree of transparency of the thermal-range image overlaid on top of the visible-range one, for example, to provide a possibility to convey information in both visible-range and thermal-range modalities simultaneously.

Figure 16:
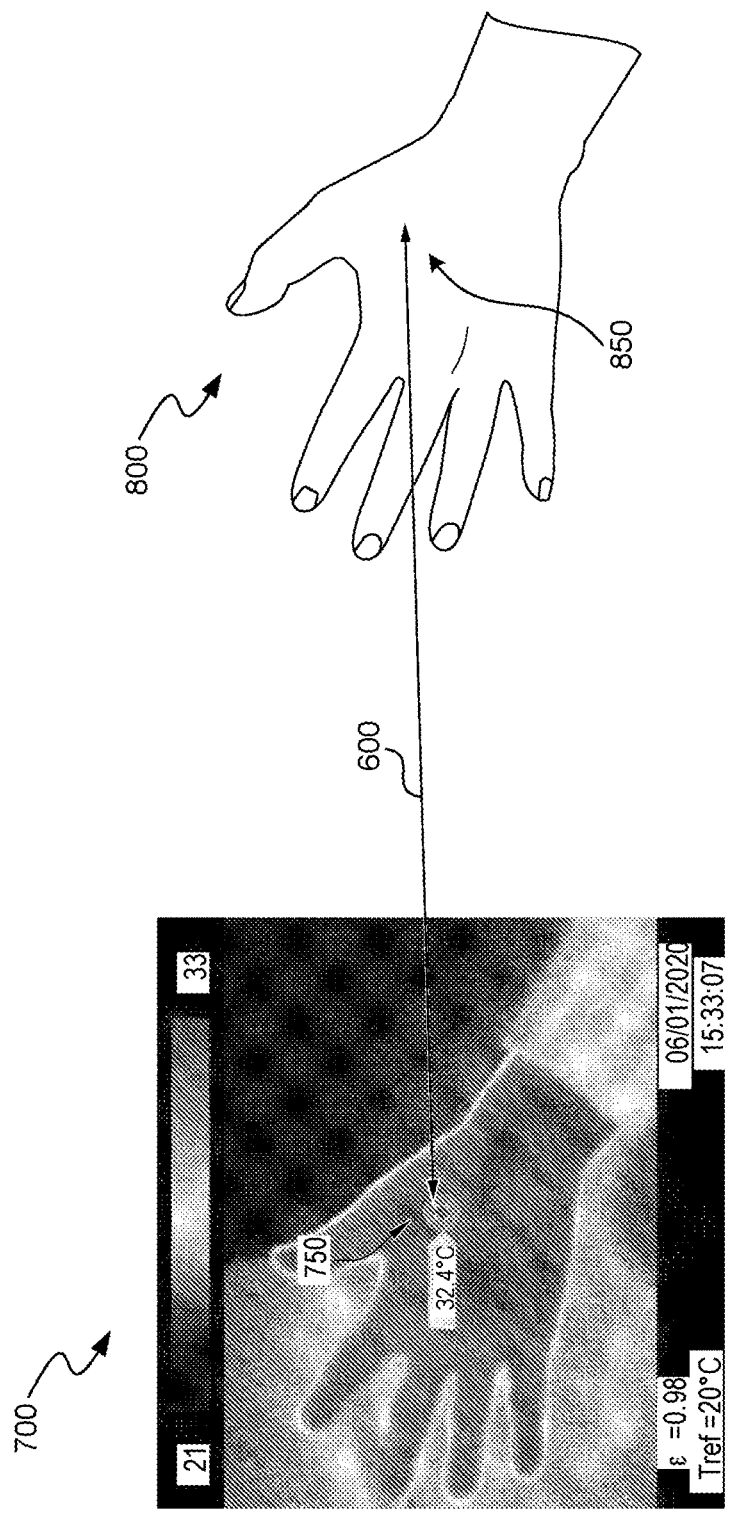
FIG. 16 shows an example illustration of an image alignment procedure according to the technology disclosed in this patent application.

FIG. 16 shows an image 700 acquired by a thermal-range camera of an endoscope according to an embodiment of the technology disclosed in the present patent application and a visible-range image 800 acquired by a visible-range camera of the endoscope after performing an image alignment procedure described above. Line 600 connects corresponding areas in the visible-range image and the thermal-range image which were aligned during the image alignment procedure.

After the images are aligned, software can allow a user to click on a region or select a region in a visible-range image of the target area and, in response to the click or the selection, the software will display a part of the thermal-range image corresponding to the region of the visible-range image. The part of the thermal-range image can be shown as overlaid on the visible-range image, for example.

Figure 17:
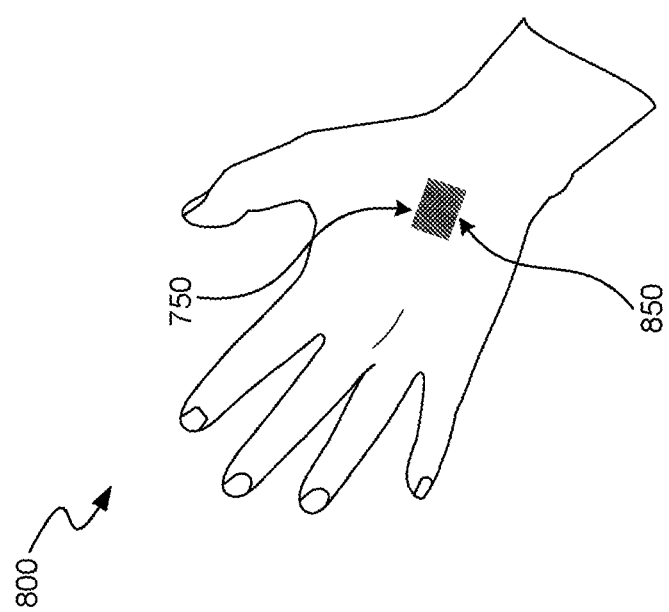
FIG. 17 shows an example illustration of a software which can display thermal-range image data overlaid on a visible-range image according to the technology disclosed in this patent application.

FIG. 17 shows that when a user clicks on the area 850 or selects the area 850 of the visible-range image 800, the area 750 of the thermal-range image 700 is displayed as overlaid on top of the area 850. Area 750 of the thermal-range image was aligned with the area 850 of the visible-range image during an image alignment procedure (e.g., the one described above).

Methods of image processing according to some embodiments of the technology disclosed in this patent document can include determining temporal evolution of the temperature of one or more regions of an area of interest (e.g., tongue or throat of a patient).

Figure 18:
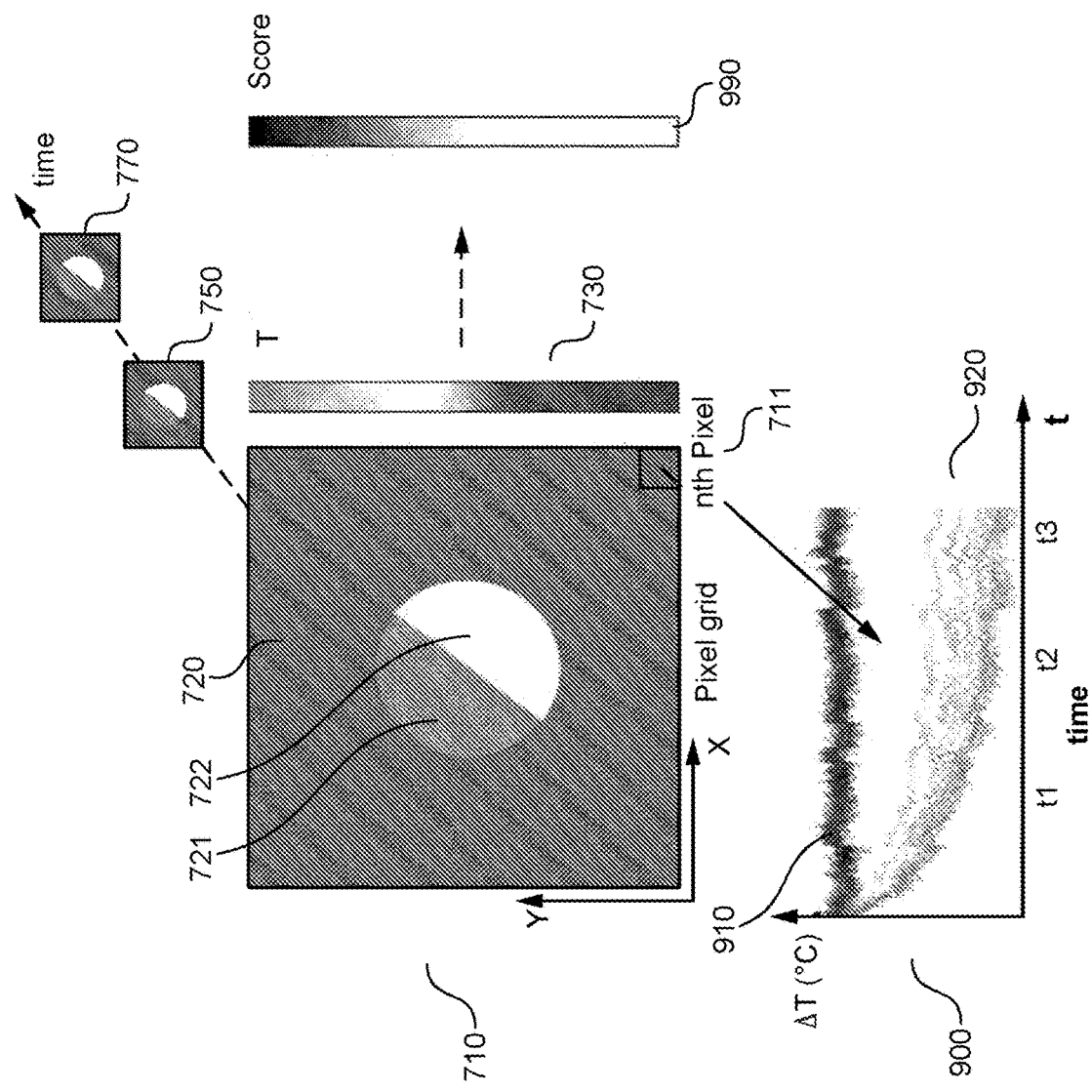
FIG. 18 shows an example illustration of thermal-range image data processing according to the technology disclosed in this patent application.

FIG. 18 shows image 710 captured by a thermal-range camera of an endoscope according to an embodiment of the technology disclosed herein. Image 710 corresponds to time point t1. Target area of interest 720 captured in the image 710 has two regions: 721 and 722. Color of pixels of the thermal image 710 can be calibrated to correspond to the temperature values of the elements of a scene captured in the image, wherein each pixel of the image corresponds to an element of the scene. Color scale 730 which can be displayed proximate to the image 720 by a software illustrates that correspondence.

Plot 900 in FIG. 18 shows evolution of the temperature values corresponding to the pixels of the image 710 in time. In particular, plot 900 shows for a number of pixels or for all pixels of the image 710, changes of the temperature values corresponding to the pixels at time t relative to the temperature values at an initial time t0. Therefore, all curves shown in plot 900 originate from the same point (0; 0) in the (time; ΔT) coordinates where ΔT is the temperature difference.

As shown in FIG. 18, temperatures corresponding to the pixels in the region 721 remained relatively constant over time, as illustrated by the curves 910 in the plot 900 corresponding to those pixels. As shown in FIG. 18, temperatures corresponding to the pixels in the region 722 exhibited various rates of decrease over time, as illustrated by the curves 920 in the plot 900 corresponding to the pixels in the region 722 of the target area 720.

Images 750 and 770 shown in FIG. 18 correspond to time points t2 and t3 such that t1<t2<t3. As discussed above, based on the temperature information captured in the thermal-range images and/or based on the temperature dynamics information captured in the sequences of the thermal-range images, a score value can be assigned to a thermal-range image and/or to an area of interest in the thermal-range image which would reflect a likelihood of the observed temperature in the area of interest and/or the observed temperature change in the area of interest being, for example, abnormal or otherwise clinically significant. For example, the score can indicate a likelihood of an inflammation in the area of interest.

Thermographic imaging capability of the embodiments of the technology disclosed in this patent document provides additional information to what is available through visual inspection. When implemented in an embodiment of the disclosed technology, thermographic imaging can provide information about the temperature patterns of ENT areas, enabling sub-surface imaging and higher contrast imaging of abnormal conditions in a patient which are accompanied by alterations of thermal properties of tissues or organs. Asymmetric muscular activity and skin conditions (e.g., inflammation, infection, lesions of various nature), together with the evolution of such pathologies and treatment, can be monitored, processed, and recorded as well.

Embodiments of the presently disclosed technology enable development of effective imaging tools to assist ENT clinicians to obtain thermographic imaging and perform sub-surface detection of ENT conditions. The presently disclosed technology can lead to development and improvement of ENT diagnosis and surgery, endoscopic surgeries, telemedicine, point of care diagnostics, and medical education.

Example Technical Solutions

The following examples may be preferable features of possible implementations of an endoscope according to the technology disclosed in this patent application.

Example 1 includes an endoscope which has a body having a proximal end and a distal end.

Example 2 includes the endoscope of Example 1 which comprises a visible-range camera attached proximate to the proximal end of the endoscope body.

Example 3 includes the endoscope of Example 2 wherein the visible-range camera is removably attached to the endoscope body.

Example 4 includes the endoscope as in any of Examples 1-3 which comprises an endoscope mirror attached proximate to the distal end of the endoscope body.

Example 5 includes the endoscope of Example 4 wherein the endoscope mirror is pivotably attached to the endoscope body.

Example 6 includes the endoscope as in any of Examples 4 or 5 wherein the endoscope mirror is removably attached to the endoscope body.

Example 7 includes the endoscope as in any of Examples 1-6 which comprises a thermal-range camera.

Example 8 includes the endoscope as in Example 7 wherein the thermal-range camera is attached proximate to the proximal end of the endoscope body.

Example 9 includes the endoscope as in Example 7 wherein the thermal-range camera is attached proximate to the distal end of the endoscope body.

Example 10 includes the endoscope as in any of Examples 7-9 wherein the thermal-range camera can capture images using light in a range of wavelengths from the range between 8 μm and 14 μm.

Example 11 includes the endoscope as in any of Examples 1-10 which comprises a light source attached proximate to the proximal end of the endoscope body.

Example 12 includes the endoscope of Example 11 wherein the light source can emit light in a range of wavelengths from the range between 380 nm and 740 nm.

Example 13 includes the endoscope of Example 11 wherein the light source can emit light on one or more wavelengths from any of the following ranges: 380-450 nm, 450-485 nm, 485-500 nm, 500-565 nm, 565-590 nm, 590-625 nm, or 625-740 nm.

Example 14 includes the endoscope as in any of Examples 2-13 wherein the visible-range camera can register an image using light on one or more wavelengths from the range of wavelengths between 380 nm and 740 nm.

Example 15 includes the endoscope as in any of Examples 1-14 which comprises one or more optical elements inside the endoscope body which relay and/or magnify an image transmitted by light within the endoscope body.

Example 16 includes the endoscope of Example 15 wherein at least one optical element of the one or more optical elements is a lens or a set of two or more lenses.

Example 17 includes the endoscope as in any of Examples 11-16 wherein light from the light source is delivered to the endoscope mirror using at least one of a beam splitter housed inside the endoscope body or one or more optical fibers either housed inside the endoscope body or at least partially disposed outside the endoscope body.

Example 18 includes the endoscope as in any of Examples 11-17 wherein the endoscope mirror is configured to reflect at least a part of the light received by the endoscope mirror from the light source to a target area.

Example 19 includes the endoscope as in any of Examples 4-18 wherein the endoscope mirror is configured to direct at least a part of the light reflected from an area of interest or emitted by the area of interest towards at least one of the visible-range camera or the thermal-range camera.

Example 20 includes the endoscope as in any of Examples 7-19 which comprises a second mirror configured to at least partially reflect light in a wavelength band from the range between 8 µm and 14 µm towards the thermal-range camera and configured to at least partially transmit light in a wavelength band from the range between 380 nm and 740 nm towards the visible-range camera.

Example 21 includes the endoscope as in Example 20 wherein the second mirror is positioned between the optical elements and the visible-range camera.

Example 22 includes the endoscope as in any of Examples 1-21 which comprises a thermal imager.

Example 23 includes the endoscope as in Example 22 wherein the thermal imager has a body which has a proximal end and a distal end.

Example 24 includes the endoscope as in Example 22 wherein the thermal imager is a second thermal-range camera.

Example 25 includes the endoscope as in any of Examples 22-24 wherein the thermal imager is attached to the body of the endoscope proximate to the distal end of the endoscope body.

Example 26 includes the endoscope as in Example 23 wherein the thermal imager is attached to the endoscope body such that the distal end of the thermal imager is closer to the distal end of the endoscope body than the proximal end of the thermal imager.

Example 27 includes the endoscope as in Example 26 which comprises an imager mirror attached proximate to the distal end of the thermal imager body.

Example 28 includes the endoscope of Example 27 in which the imager mirror is pivotably attached to the thermal imager body.

Example 29 includes the endoscope as in any of Examples 27-28 wherein the imager mirror is removably attached to the thermal imager body.

Example 30 includes the endoscope as in any of Examples 27-29 which comprises an imager thermal-range camera.

Example 31 includes the endoscope as in Example 30 wherein the imager thermal-range camera is attached proximate to the proximal end of the thermal imager body.

Example 32 includes the endoscope as in Example 30 in which the imager thermal-range camera can capture images using light in a range of wavelengths from the range between 8 µm and 14 µm.

Example 33 includes the endoscope as in Example 24 in which the second thermal-range camera can capture images using light in a range of wavelengths from the range between 8 µm and 14 µm.

Example 34 includes the endoscope as in any of Examples 27-32 which comprises one or more optical elements inside the thermal imager body which relay and/or magnify an image transmitted by light propagating between the imager mirror and the imager thermal-range camera.

Example 35 includes the endoscope of Example 34 wherein at least one optical element of the one or more optical elements is a lens or a set of two or more lenses.

Example 36 includes the endoscope of Example 24 wherein the second thermal camera is configured to receive light reflected by a mirror.

Example 37 includes the endoscope of Example 24 wherein the second thermal camera is configured to receive light directly from an area of interest.

Example 38 includes the endoscope of Example 24 wherein the endoscope comprises a third endoscope mirror attached to the endoscope body proximate to the distal end of the endoscope body, wherein the second thermal camera is configured to receive light reflected by the third endoscope mirror.

Example 39 includes the endoscope of Example 1 comprising a third thermal-range camera attached proximate to the distal end of the endoscope body.

Example 40 includes the endoscope as in any of Examples 1-39 wherein the body of the endoscope is rigid.

Example 41 includes the endoscope as in any of Examples 1-39 wherein the body of the endoscope is flexible and/or bendable.

Example 42 includes the endoscope as in Example 39 comprising a fourth mirror attached to the body of the endoscope proximate to the distal end of the endoscope body.

Example 43 includes the endoscope as in Example 42 wherein the third thermal-range camera is at least partially enclosed by the endoscope body.

Example 44 includes the endoscope as in any of Examples 42-43 wherein the third thermal-range camera is configured to receive at least a portion of the light reflected by the fourth mirror.

Example 45 includes the endoscope as in any of Examples 1-44 comprising a data processor.

Example 46 includes the endoscope as in Example 45 wherein the data processor comprises at least one of a memory, a processor, or a communication interface.

Example 47 includes the endoscope as in Example 46 wherein the processor is communicatively coupled to at least one of the memory or the communication interface.

Example 48 includes the endoscope as in any of Examples 45-47 wherein the data processor is communicatively coupled to at least one of the visible-range camera or the thermal-range camera.

Example 49 includes the endoscope as in any of Examples 45-48 wherein the data processor is included into the visible-range camera.

Example 50 includes the endoscope as in any of Examples 45-49 comprising a second data processor.

Example 51 includes the endoscope as in Example 50 wherein the second data processor comprises at least one of a second memory, a second processor, or a second communication interface.

Example 52 includes the endoscope as in Example 51 wherein the second processor is communicatively coupled to at least one of the second memory or the second communication interface.

Example 53 includes the endoscope as in any of Examples 50-52 wherein the second data processor is communicatively coupled to at least one of the visible-range camera or the thermal-range camera.

Example 54 includes the endoscope as in any of Examples 50-53 wherein the second data processor is included into the thermal-range camera.

Example 55 includes the endoscope as in any of Examples 50-54 wherein the data processor is communicatively coupled to the second data processor.

Example 56 includes the endoscope as in any of Examples 46-55 wherein the communication interface provides communication between the data processor and a computer via at least one of USB, Ethernet, serial, parallel, or Bluetooth interfaces.

Example 57 includes the endoscope as in any of Examples 51-56 wherein the second communication interface provides communication between the second data processor and a computer via at least one of USB, Ethernet, serial, parallel, or Bluetooth interfaces.

Example 58 includes the endoscope as in any of Examples 56-57 wherein the computer is a cloud-based or remote computer.

Example 59 includes the endoscope as in any of Examples 56-58 wherein the data processor and/or the second data processor are used to transfer raw or processed images or video streams between at least one of the visible-range camera or the thermal-range camera and the computer.

Example 60 includes the endoscope as in any of Examples 1-59 which comprises a power source or an interface to a power source.

Example 61 includes the endoscope as in Example 60 wherein the power source is a rechargeable battery.

Example 62 includes the endoscope as in Example 61 wherein the rechargeable battery is housed within at least one of the body of the endoscope, the visible-range camera, the thermal-range camera, or the thermal imager.

Example 63 includes the endoscope as in Example 60 wherein the interface to a power source is a power connector.

Example 64 includes the endoscope as in any of Examples 1-63 wherein a tilt angle between the endoscope mirror and the endoscope body is adjustable.

Example 65 includes the endoscope as in any of Examples 1-64 wherein a tilt angle between the imager mirror and the imager body is adjustable.

Example 66 includes the endoscope as in any of Examples 1-65 wherein a tilt angle between the third endoscope mirror and the endoscope body is adjustable.

Example 67 includes the endoscope as in any of Examples 1-66 wherein a tilt angle between the fourth mirror and the endoscope body is adjustable.

Example 68 includes the endoscope as in any of Examples 7-67 which comprises a second mirror configured to at least partially reflect light in a wavelength band from the range between 380 nm and 740 nm towards the visible-range camera and configured to at least partially transmit light in a wavelength band from the range between 8 μm and 14 μm towards the thermal-range camera.

It is intended that the specification, together with the drawings, be considered exemplary only, where exemplary means an example. As used herein, the singular forms "a", "an" and "the" are intended to include the plural forms as well, unless the context clearly indicates otherwise. Additionally, the use of "or" is intended to include "and/or", unless the context clearly indicates otherwise.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described, and other implementations, enhancements and variations can be made based on what is described and illustrated in this patent document.

What is claimed is:
1. An endoscope, comprising:
   a body having a proximal end and a distal end;
   a light source configured to emit light in a first range of wavelengths and attached to the body proximate to the proximal end of the body;
   a first mirror attached to the body proximate to the distal end of the body;
   a first imaging system attached to the body proximate to the proximal end of the body;
   a second imaging system attached to the body proximate to the distal end of the body; and
   a second mirror pivotably attached to the body proximate to the distal end of the body and configured to direct light emitted by a target area in a second range of wavelengths into the second imaging system,
   wherein:
      the first mirror is configured to reflect light received by the first mirror from the light source towards the target area, and configured to receive a first portion of light in the first range of wavelengths reflected by the target area and direct the first portion of light towards the proximal end of the body,
      the first imaging system is configured to receive at least a part of the first portion of light and create a first image of the target area corresponding to the first range of wavelengths, and
      the second imaging system is configured to receive the light emitted by the target area in the second range of wavelengths and create a second image of the target area corresponding to the second range of wavelengths.

2. The endoscope as in claim 1, wherein the first imaging system is a video camera configured to create an image using light in the first range of wavelengths.

3. The endoscope as in claim 1, wherein the first imaging system is an optical system configured to create an image in an image plane using light in the first range of wavelengths.

4. The endoscope as in claim 1, wherein the second imaging system is a video camera configured to create an image using light in the second range of wavelengths.

5. The endoscope as in claim 1, wherein the second imaging system is an optical system configured to create an image in an image plane using light in the second range of wavelengths.

6. The endoscope as in claim 1, wherein the first range of wavelengths comprises one or more wavelengths between 380 nm and 740 nm.

7. The endoscope as in claim 1, wherein the second range of wavelengths comprises one or more wavelengths between 8 micrometers and 14 micrometers.

8. The endoscope as in claim 1, wherein the first mirror is pivotably attached to the body.

9. The endoscope as in claim 1, wherein at least one of the first mirror or the second mirror is removably attached to the body.

10. The endoscope as in claim 1, wherein the body is rigid.

11. The endoscope as in claim 1, wherein the body is bendable.

12. A method of fabrication of an endoscope, comprising:
providing a body having a proximal end and a distal end;
coupling a light source capable of producing light in a first wavelength band to the body proximate to the proximal end of the body;
coupling a first mirror to the body proximate to the distal end of the body;
coupling a first imaging system to the body proximate to the proximal end of the body;
coupling a second imaging system to the body proximate to the distal end of the body; and
pivotably attaching a second mirror to the body proximate to the distal end of the body, wherein the second mirror is capable of directing light emitted by a target area in a second wavelength band into the second imaging system,
wherein:
the first mirror is configured to reflect light received by the first mirror from the light source towards the target area, the first mirror being further capable of receiving a first portion of light in the first wavelength band reflected by the target area and directing the first portion of light towards the proximal end of the body,
the first imaging system is configured to receive at least a part of the first portion of light and create a first image of the target area corresponding to the first wavelength band, and
the second imaging system is configured to receive the light emitted by the target area in the second wavelength band and create a second image of the target area corresponding to the second wavelength band.

13. The method of fabrication of an endoscope as in claim 12, wherein the first imaging system is a video camera capable of creating an image using light in the first wavelength band.

14. The method of fabrication of an endoscope as in claim 12, wherein the first imaging system is an optical system capable of creating an image in an image plane using light in the first wavelength band.

15. The method of fabrication of an endoscope as in claim 12, wherein the second imaging system is a video camera capable of creating an image using light in the second wavelength band.

16. The method of fabrication of an endoscope as in claim 12, wherein the second imaging system is an optical system capable of creating an image in an image plane using light in the second wavelength band.

17. The method of fabrication of an endoscope as in claim 12, wherein the first wavelength band comprises one or more wavelengths between 380 nm and 740 nm.

18. The method of fabrication of an endoscope as in claim 12, wherein the second wavelength band comprises one or more wavelengths between 8 micrometers and 14 micrometers.

19. The method of fabrication of an endoscope as in claim 12, wherein coupling the first mirror to the body comprises removably attaching the first mirror to the body.

20. The method of fabrication of an endoscope as in claim 12, wherein pivotably attaching the second mirror to the body comprises removably attaching the second mirror to the body.

* * * * *